United States Patent
Kim et al.

(10) Patent No.: US 9,657,312 B2
(45) Date of Patent: May 23, 2017

(54) REPLICATION COMPETENT PSEUDO-TYPE RETROVIRUS VECTOR SYSTEM

(75) Inventors: Yeon Soo Kim, Seoul (KR); Moon Kyung Kang, Daejeon (KR); A Young Song, Ulsan (KR)

(73) Assignee: Inje University Industry-Academic Cooperation Foundation, Gimhae-si, Gyeongsangnam-Do (KR)

(*) Notice: Subject to any disclaimer, the term of this patent is extended or adjusted under 35 U.S.C. 154(b) by 0 days.

(21) Appl. No.: 14/384,687

(22) PCT Filed: Mar. 13, 2012

(86) PCT No.: PCT/KR2012/001818
§ 371 (c)(1),
(2), (4) Date: Jan. 15, 2015

(87) PCT Pub. No.: WO2013/137495
PCT Pub. Date: Sep. 19, 2013

(65) Prior Publication Data
US 2015/0176026 A1    Jun. 25, 2015

(30) Foreign Application Priority Data

Mar. 12, 2012  (KR) .................. 10-2012-0025008
Mar. 12, 2012  (KR) .................. 10-2012-0025009

(51) Int. Cl.
*C12N 15/86*  (2006.01)
*A61K 35/76*  (2015.01)
(Continued)

(52) U.S. Cl.
CPC .............. *C12N 15/86* (2013.01); *A61K 35/76* (2013.01); *A61K 38/162* (2013.01); *A61K 38/45* (2013.01);
(Continued)

(58) Field of Classification Search
None
See application file for complete search history.

(56) References Cited

U.S. PATENT DOCUMENTS 6,589,763 B1    7/2003    Von Laer et al.
8,034,335 B2    10/2011   Caruso et al.

OTHER PUBLICATIONS

Schambach et al. Chapter 14: Design and Production of Retro- and Lentiviral Vectors for Gene Expression in Hematopoietic Cells, in Methods in Molecular Biology, Methods and Protocols, vol. 506, Christopher Baum (ed.), © Humana Press a part of Springer Science + Business Media, LLC 2009.*

(Continued)

*Primary Examiner* — Janet L Andres
*Assistant Examiner* — Stuart W Snyder
(74) *Attorney, Agent, or Firm* — Revolution IP, PLLC

(57) ABSTRACT

The present invention provides a vector system in which a MuLV-Gag gene, a MuLV-Pol gene, and a GaLV-Env gene are expressed in two separate vectors. The vector system is capable of inserting a therapeutic gene to these two separate vectors, and in this raged, the size of an inserted gene is not limited and a variety of foreign therapeutic genes may be inserted to the vectors. Accordingly, the foreign therapeutic gene may be delivered in a safe and efficient manner to desired tissue of cells of aberrant proliferation. Therefore, the vector system is applicable in a composition for delivering a gene targeting the aberrantly dividing cells of aberrant proliferation, wherein the composition includes a retrovirus produced by cell line transfection. The vector system is also applicable in a composition for preventing or treating a disease caused by cells of aberrant proliferation of, such as cancer cells.

11 Claims, 14 Drawing Sheets

(51) Int. Cl.
    *A61K 38/16*    (2006.01)
    *A61K 38/45*    (2006.01)
    *A61K 48/00*    (2006.01)

(52) U.S. Cl.
    CPC .... *A61K 48/00* (2013.01); *C12N 2740/10032* (2013.01); *C12N 2740/10043* (2013.01); *C12N 2740/13045* (2013.01); *C12N 2740/13052* (2013.01); *C12N 2800/40* (2013.01); *C12N 2800/50* (2013.01); *C12Y 207/01021* (2013.01)

(56) References Cited

OTHER PUBLICATIONS

Miller et al. Construction and Properties of Retrovirus Packaging Cells Based on Gibbon Ape Leukemia Virus. J. Virol. 1991; 65(5): 2220-2224.*

Johann et al. GLVR1, a Receptor for Gibbon Ape Leukemia Virus, Is Homologous to a Phosphate Permease of Neurospora crassa and Is Expressed at High Levels in the Brain and Thymus. J. Virol. 1992; 66(3): 1635-1640.*

Qiao et al. VSV-G pseudotyped, MuLV-based, semi-replication competent retrovirus for cancer treatment. Gene Ther. 2006; 13: 1457-1470.*

"HeLa ATCC® CCL-2™ Homo sapiens cervix adenocarcinoma" product sheet downloaded Apr. 15, 2016.*

Solly et al. Replicative retroviral vectors for cancer gene therapy. Canc. Gene Ther. 2003; 10: 30-39.*

Qiao, J. et al., "VSV-G pseudotyped, MuLV-based, semi-replication competent retrovirus for cancer treatment.", Gene Therapy vol. 13, pp. 1457-1470 (May 25, 2006).

Chen, J. et al., "Safety testing for replication-competent retrovirus associated with gibbon ape leukemia virus-pseudotyped retroviral vectors.", Human Gene Therapy vol. 12, pp. 61-70 (Jan. 1, 2001).

* cited by examiner

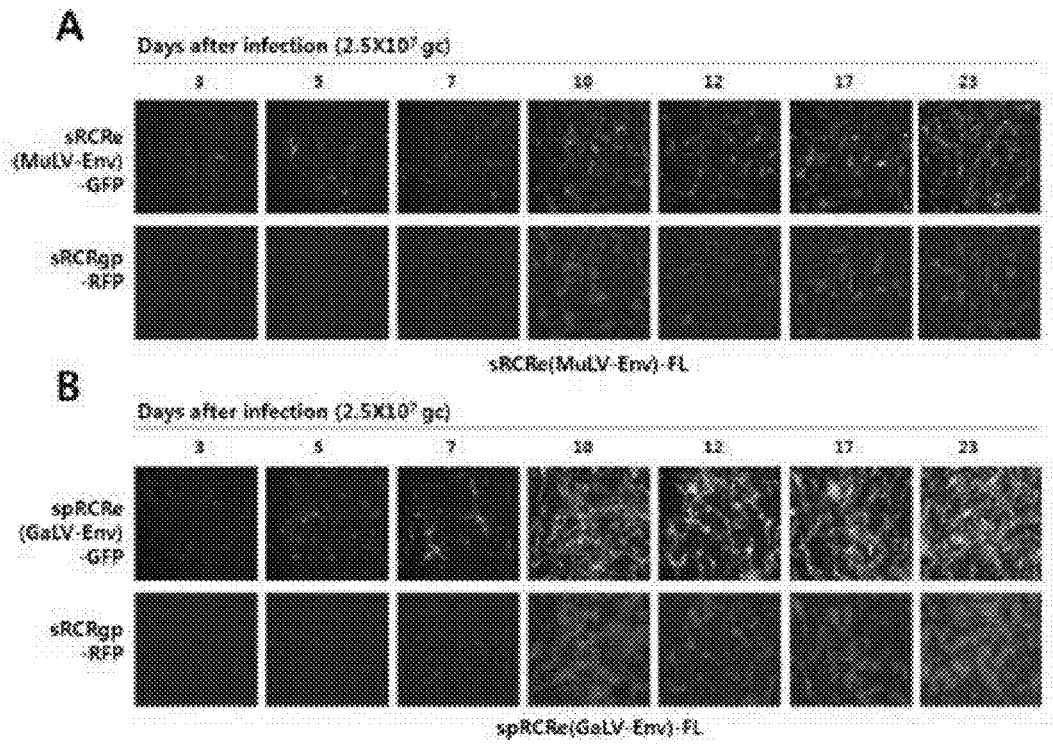

FIG. 15
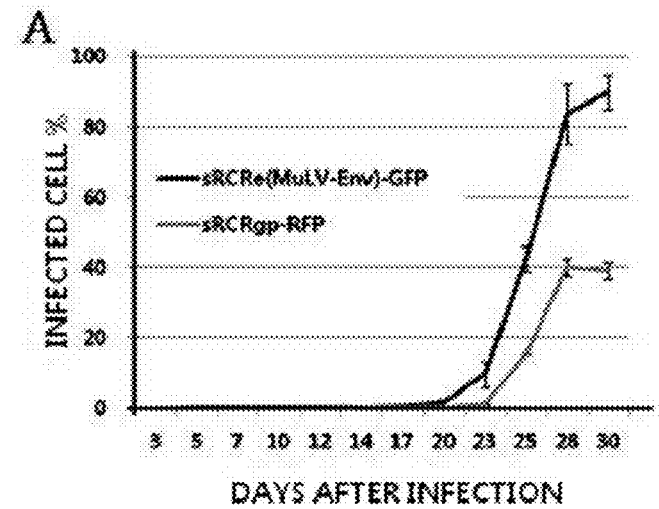
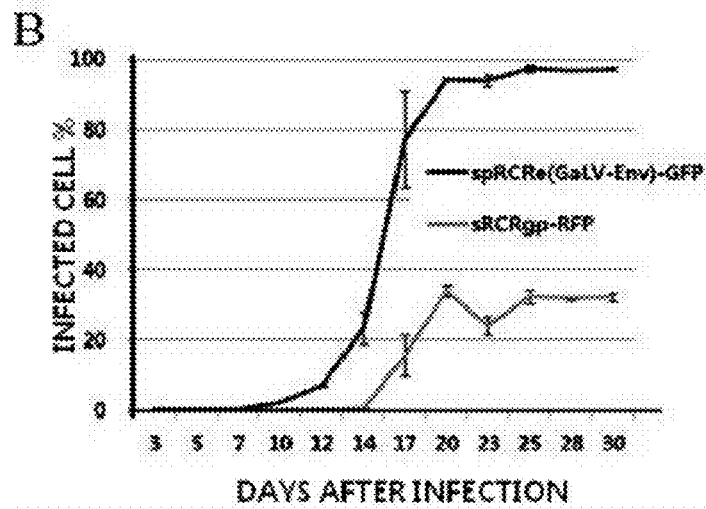
FIG. 16
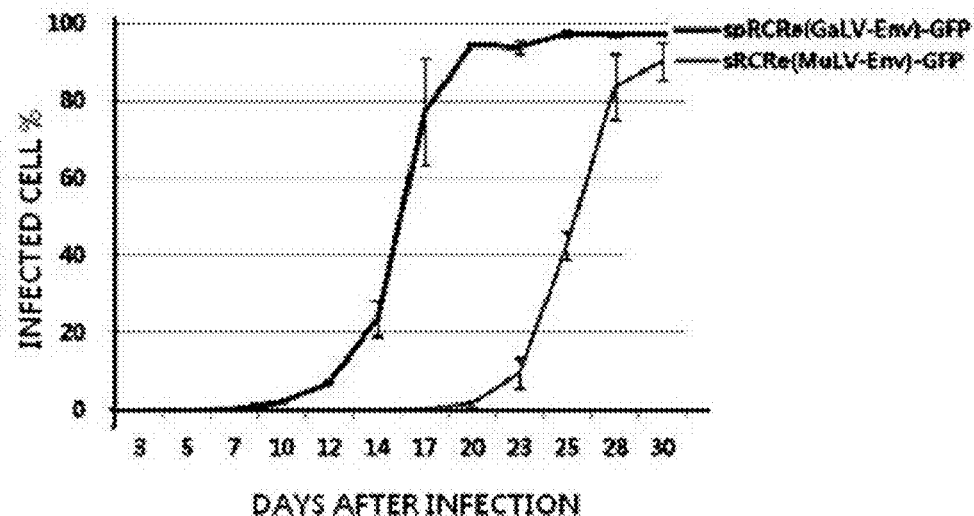

REPLICATION COMPETENT PSEUDO-TYPE RETROVIRUS VECTOR SYSTEM

CROSS REFERENCE TO PRIOR APPLICATIONS

This application is the 35 U.S.C. 371 national stage of International application PCT/KR2012/001818 filed on Mar. 13, 2012; which claims priority to Korean applications 10-2012-0025008 and 10-2012-0025009, both filed on Mar. 12, 2012. The entire contents of each of the above-identified applications are hereby incorporated by reference.

TECHNICAL FIELD

The present invention relates to a pseudotyped replication-competent retrovirus vector system capable of gene delivery in an efficient manner to dividing cells of aberrant proliferation, and to use of the pseudotyped replication-competent retrovirus vector system.

BACKGROUND ART

Proliferation occurs by the development of cells through the cell cycle characterized by the division of one cell into two cells. The cell cycle consists of 5 phases: $G_0$ phase, $G_1$ phase, S phase, $G_2$ phase, and M phase. During the $G_0$ phase, cells are quiescent and most cells in the body are in this phase. During the $G_1$ phase, cells respond to signals to divide, and produce RNA and proteins necessary for DNA synthesis. During the S phase (SE, early S-phase; SM, middle S-phase; and SL, late S-phase), cells replicate their DNA. During the $G_2$ phase, cells continue to grow and protein synthesis occurs in preparation for mitosis. During the mitotic (M) phase, a single cell divides into two daughter cells. Cells of aberrant proliferation, such as a case of cancer, are generated by alterations in the cell cycle described above, and the alterations may result from over-expression of genes, mutation of regulatory genes, or defects in DNA damage checkpoints.

There are many types of diseases related to the cells of aberrant proliferation, and representative diseases may occur due to carcinogenesis, cancer, bacterial infection, immunological rejection of transplanted organs, viral infection, autoimmune disease (for example, arthritis, lupus, inflammatory bowel disease, Sjogren's syndrome, multiple sclerosis, and the like), or combinations thereof. The most widely known, representative disease related to the cells of aberrant proliferation is cancer.

In general, cancer broadly refers to various diseases characterized by proliferation of disease cells caused by abnormal cell division. The characteristics that are consistent with all the known types of cancer include abnormal occurrence in genetic materials of cancer cells and descendant cells of the cancer cells. When cells become cancerous, the cells proliferate regardless of normal limitation, and invade and destroy adjacent tissues. In addition, through a process called metastasis, the cells may spread to an anatomical distal region.

Meanwhile, about 2,000 cases related to clinical trials of gene therapy have been permitted and carried out over the past 25 years. However, in recent years, in contrast to what has been reported as successful gene therapy for genetic disorders caused by some single-gene deletions, gene therapy for cancer is not successfully done as much as expected, regardless of the greatest number of data related to clinical trials of gene therapy in cancer fields. In addition, the anti-cancer gene therapy using an oncolytic adenovirus vector, which had great expectations some years ago, now only shows limited therapeutic effects in some types of head and neck cancer.

A common awareness regarding the cause of such a low gene therapy effect for cancer is that it is urgent to develop a vector that is capable of delivering therapeutic genes in an efficient manner to cancerous tissues. Actually, according to the clinical trials of cancer gene therapy in the past, the gene delivery efficiency with respect to cancer cells is found to be less than 1% of cancer cells with respect to the entire cancerous tissues. In order to improve such inefficient gene delivery with respect to the cancerous tissues, various types of oncolytic viruses had been developed and studied. However, due to inflammation induced by immunogenicity, rapid viral clearance, difficulties in developing a virus having a complicated gene structures, and transformation and inactivation of viruses in the body, it fails to obtain expected effects.

However, starting with the recent cancer gene therapy using an oncolytic vaccinia virus and showing highly desired clinical trial results as compared with the past clinical trial results, cancer gene therapy using a replication-competent retrovirus (RCR) has been approved in the United States in 2010. Accordingly, it is currently in a situation that a phase 1 clinical trial has been completed in 2011 and a phase 2 clinical trial is being studied. In this regard, studies for developing practical use and clinical trials of the vector system are expected to increase in the future.

DETAILED DESCRIPTION OF THE INVENTION

Technical Problem

The present invention provides a pseudotyped replication-competent retrovirus vector system including: a first recombinant expression vector carrying a Murine Leukemia virus (MuLV)-Gag gene and a MuLV-Pol gene; and a second recombinant expression vector carrying a Gibbon Ape Leukemia Virus (GaLV)-Env gene.

The present invention provides a retrovirus produced by transfecting a cell line with the vector system.

The present invention provides a composition including the retrovirus for delivering genes targeting cells of aberrant proliferation.

The present invention provides a composition for preventing and treating cancer, the composition including the retrovirus that is produced by transfecting a cell strain with the vector system to which a gene for cancer therapy is inserted as a therapeutic gene for the cells of aberrant proliferation.

In addition, the present invention provides a method of manufacturing a pseudotyped replication-competent retrovirus vector system, the method including: preparing a first recombinant expression vector carrying a MuLV-Gag gene and a MuLV-Pol gene; and preparing a second recombinant expression vector carrying a GaLV-Env gene.

Technical Solution

According to aspects of the present invention, there are provided a vector system in which a MuLV-Gag gene, a MuLV-Pol gene, and a GaLV-Env gene are expressed in two separate vectors, a retrovirus produced by transfecting a cell line with the vector system, a composition including the retrovirus for delivering genes targeting cells of aberrant proliferation, a composition for preventing and treating cancer, and a method of manufacturing a vector system in which a MuLV-Gag gene, a MuLV-Pol gene, and a GaLV-Env gene are expressed in two separate vectors.

Hereinafter, the present invention is described in detail.

The most widely known cells of aberrant proliferation in the art are cancer cells, and thus, the vector system of the present invention targets the cancer cells that continuously divide throughout experiments. In cancer gene therapy, the efficiency of delivering a defective retrovirus vector to the cancer cells is less than 1% of the cancer cells with respect to the entire cancerous tissues. In this regard, a replication-competent retrovirus is used to overcome such vulnerability. However, if a vector size increases by additional insertion of a therapeutic gene into a genome of a wild-type retrovirus, there may be problems with loss of the therapeutic function upon genetic recombination of the vector and decrease of packaging efficiency. While making efforts to solve such problems, it is confirmed that the vector system of the present invention is applicable to all types of the cells of aberrant proliferation based on features that the vector system of the present invention is less restricted in size of an inserted gene and has good efficiency of gene delivery to the cancer cells. It is particularly confirmed in an animal model that the gene delivery to cancerous tissues occurs in all the dividing cancerous tissues.

The present invention provides a first recombinant expression vector carrying a Murine Leukemia virus (MuLV)-Gag gene and a MuLV-Pol gene; and a second recombinant expression vector carrying a Gibbon Ape Leukemia Virus (GaLV)-Env gene.

The first recombinant expression vector carries the MuLV-Gag gene and the MuLV-Pol gene, but is not limited thereto. The first recombinant expression vector may be a vector having a plasmid map of FIG. 1.

The second recombinant expression vector carries the GaLV-Env gene, but is not limited thereto. The second recombinant expression vector may be a vector having a plasmid map of FIG. 2.

A replication-competent retrovirus (RCR) vector is a nonlytic viral vector so that there will be no occurrence of cell damage when virus vectors are released. In addition, an antibody specific to the virus vectors is not generated so that there will be no occurrence of viral clearance, and in this regard, the RCR vector is considered as an excellent gene carrier.

The replication-competent characteristics may refer to capability of producing virus particles in an infected or transformed cell obtained by transfecting a particular viral gene with an animal cell having high susceptibility to the viral gene or by infecting the animal cell with the viral gene.

The RCR enters a nucleus when a nuclear membrane breaks down, and accordingly, infects only dividing cells. That is, the RCR may specifically infect dividing cells of aberrant proliferation, such as cancer cells. In this regard, the RCR prevents an inserted gene from being expressed in other normal cells and provides safety of the gene delivery to the cells of aberrant proliferation. In addition, since the RCR is a virus capable of replication, the efficiency of the gene deliver may be also increased.

The gag gene may be a polyprotein consisting four types of a retrovirus core, the pol gene may be a reverse transcriptase, and the env gene may be an envelope glycoprotein.

In the present invention, the env gene of the retrovirus is replaced with GaLV-Env gene so that the virus proliferation and the efficiency of the gene delivery may be improved.

In an exemplary embodiment, in manufacturing and comparing the second recombinant expression vectors, such as an sRCR vector carrying a MuLV-Env gene and a spRCR vector carrying a GaLV-Env gene, the expression vector carrying the GaLV-Env gene is resulted with high rates of the virus infection and good efficiency of the gene delivery.

In another exemplary embodiment, when the vectors are infected with high-titer and left for 12 days, it is found that the vector carrying the MuLV-Env gene has an infection rate remained at about 80% while the vector carrying the GaLV-Env gene has an infection rate approaching almost 100%. Alternatively, when the vectors are infected with low-titer and left for 20 days, it is found that the vector carrying the MuLV-Env genes has an infection rate of only about 2% while the vector carrying the GaLV-Env genes has an infection rate of about 94%.

In another exemplary embodiment, in the first day of the treatment that an apoptosis-related gene is introduced to the vectors and the vectors are treated with a precursor drug GCV in concentration of 10 µg/ml, it is found that the number of the cells infected with a sRCR-TK vector is reduced by 40% while the number of the cells infected with a spRCR-TK vector is reduced by 60%.

In another exemplary embodiment, in comparison of the infection rates of the cancer cells infected with sRCR-FL and spRCR-FL vectors in vivo, it is found that the cancer cells infected with the sRCR-FL vector have very weak fluorescence brightness and include viruses that are topically infected while the cancer cells infected with the spRCR-FL vector include viruses that clearly spread overall according to the shape of the cancer cells.

In addition, the vectors may include 5'-LTR and 3'-LTR. A nucleotide sequence of an inserted gene to be delivered may be inserted between these LTRs.

The expression vector of the present invention is designed to deliver a foreign gene to the abnormally dividing cells of aberrant proliferation. Here, a foreign gene may be inserted in the first recombinant expression vector and the second recombinant expression vector.

In the expression vector of the related art, a foreign gene is additionally inserted to the original virus genome so that the size of the foreign gene for insertion is limited. However, in the vector system of the present invention, one viral vector is divided into two separate vectors so that the foreign gene may be inserted to these two separate vectors. Accordingly, a variety of genes may be inserted to the vectors without considering the size limitation, and in addition, the genes may be in good conditions for replication and proliferation as much as the conditions of the one viral vector.

The foreign gene is not particularly limited, but may be a therapeutic gene of the cells of aberrant proliferation. In some embodiments, the foreign gene may be a therapeutic gene of the cancer cells.

The cells of aberrant proliferation may generally refer to the occurrence of cell division at inappropriately high levels upon cell proliferation deviated from normal, suitable, or expected courses. In some embodiments, the cells of aberrant proliferation may include cells including damaged or deleted DNA or other cellular components that abnormally proliferate.

The foreign gene is delivered to the abnormally dividing cells of aberrant proliferation, but types of the foreign gene are not particularly limited. The foreign gene may include a hormone, an enzyme, a carrier, a reporter gene, of a therapeutic gene of the cells of aberrant proliferation therapeutic gene.

In some embodiments, in the case of inserting a therapeutic gene of the cells of aberrant proliferation to the vectors as shown in the plasmid map of FIG. 3, the therapeutic gene of the cells of aberrant proliferation may be inserted to the second recombinant expression vector.

In some embodiments, when the cells of aberrant proliferation are cancer cells, a therapeutic gene of the cancer cell may use an apoptosis-related gene, e.g., thymidine kinase (TK). In the related art, the size of TK was too large to produce effects of the existing vectors. When a large-sized gene is applied to a retrovirus, there may be a problem with occurrence of recombination and limitation of packaging. However, the vector system of the present invention is capable of accepting a large-sized foreign gene, and accordingly, the TK gene may be delivered to cancer cells without causing a problem.

The present invention provides a retrovirus produced by transfecting a cell line with the vector system.

The cell line is not particularly limited, and may include human 293 cells, hela cells, canine D17 cells, pellain PG4 cells, or the like.

The transfection may be performed according to methods known in the art including a lipopectamine method (Invitrogen company), microinjection (Capecchi, M. R., Cell, 22:479 (1980)), calcium phosphate precipitation (Graham, F. L. et al., Virology, 52:456 (1973)), electroporation (Neumann, E. et al., EMBO J., 1:841 (1982)), liposome-mediated transfection (Wong, T. K. et al., Gene, 10:87 (1980)), DEAE-dextran treatment (Gopal, Mol. Cell Biol., 5:1188-1190 (1985)), and gene bombardment (Yang et al., Proc. Natl. Acad. Sci., 87:9568-9572 (1990)), but the methods are not limited thereto.

Then, the transfected cell is cultured in a suitable medium. The medium used herein may be any one of media generally used in culturing an animal cell, and for example, may be Eagles's MEM (Eagle's minimum essential medium, Eagle, H. Science 130:432 (1959)), a-MEM (Stanner, C. P. et al., Nat. New Biol. 230:52 (1971)), Iscove's MEM (Iscove, N. et al., J. Exp. Med. 147:923 (1978)), 199 medium (Morgan et al., Proc. Soc. Exp. Bio. Med., 73:1 (1950)), CMRL 1066, RPMI 1640 (Moore et al., J. Amer. Med. Assoc. 199:519 (1967)), F12 (Ham, Proc. Natl. Acad. Sci. USA 53:288 (1965)), F10 (Ham, R. G. Exp. Cell Res. 29:515 (1963)), DMEM (Dulbecco's modification of Eagle's medium, Dulbecco, R. et al., Virology 8:396 (1959)), a mixture of DMEM and F12 (Barnes, D. et al., Anal. Biochem. 102:255 (1980)), Way-mouth's MB752/1 (Waymouth, C. J. Natl. Cancer Inst. 22:1003 (1959)), McCoy's 5A (McCoy, T. A., et al., Proc. Soc. Exp. Biol. Med. 100:115 (1959)), and MCDB series (Ham, R. G. et al., In Vitro 14:11 (1978)) in consideration of the purses. The description of the medium may be referred to the description provided in R. Ian Freshney, Culture of Animal Cells, A Manual of Basic Technique, Alan R. Liss, Inc., New York.

Accordingly, a retrovirus produced by transfecting the cell line with the vector system may be obtained from the culture that is already prepared.

The present invention provides a composition including the retrovirus for delivering genes targeting the cells of aberrant proliferation.

The target cells by the retrovirus may include all types of the abnormally dividing cells of aberrant proliferation, but are not limited thereto.

These abnormally dividing cells of aberrant proliferation may be caused a variety of diseases in the human body, such as cancer disease, inflammatory disease, or hyperproliferative vascular disorder.

The cells of aberrant proliferation may be cancer cells.

The cancer cells refer to cells that abnormally proliferate without any restriction in biological tissues and cause tumors therein. The types of the cancer cells are not particularly limited, but may include cells derived from myxoid and round cell carcinomas, locally advanced tumors, metastatic cancer, Ewing's sarcoma, cancer metastasis, lymphatic metastasis, squamous epithelial cell carcinoma, esophagus squamous epithelial cell carcinoma, oral carcinoma, multiple myeloma, acute lymphocytic leukemia, acute non-lymphocytic leukemia, chronic lymphocytic leukemia, chronic myelocytic leukemia, hairy cell leukemia, effusion lymphoma (body cavity based lymphoma), thymic lymphoma lung cancer, small cell carcinoma of the lung, cutaneous T-cell lymphoma, Hodgkin's lymphoma, non-Hodgkin's lymphoma, cancer of the adrenal cortex, ACTH-producing tumor, non-small cell carcinoma of the lung, breast cancer, small cell carcinoma, ductal carcinoma, stomach cancer, colon cancer, colorectal cancer, polyp associated with colorectal neoplasia, pancreatic cancer, liver cancer, bladder cancer, primary superficial bladder tumor, invasive transitional cell carcinomas of the bladder, muscle-invasive bladder cancer, prostate cancer, renal cell carcinoma, esophagus cancer, ovarian carcinoma, uterine cervical cancer, endometrial cancer, choriocarcinoma, ovarian cancer, primary peritoneal epithelial neoplasm, cervical carcinomas, vaginal cancer, cancer of the vulva, uterine cancer, solid tumor in the ovarian follicle, testicular cancer, penile cancer, renal cell carcinoma, brain cancer, head and neck cancer, neuroblastoma, asfrocytic brain tumor, glioma, metastatic tumor cell invasion in the central nervous system, osteoma, osteosarcoma, malignant melanoma, tumor progression of human skin keratinocyte, thyroid cancer, retinoblastoma, neuroblastoma, mesothelioma, Wilms's tumor, gall bladder cancer, trophoblastic neoplasm, hemangiopericytoma, or Kaposi's sarcoma.

The cells of aberrant proliferation may be non-cancer cells derived from an inflammatory disease or a hyperproliferative vascular disorder.

The inflammatory disease includes all of the diseases that cause inflammation by cells of aberrant proliferation. Inflammation may occur upon an immunologically competent cell that is activated in response to a reaction with a foreign organism or an antigenic protein, and such an inflammatory reaction may be generally induced by an injury or an antigen, such as a viral, bacterial, protozoal, or fungal antigen.

The types of the inflammatory disease are not particularly limited, but non-cancerous aberrantly proliferating cells derived from the inflammatory disease may include cells derived from inflammatory-induced bone disease, degenerative arthritis, diabetes, autoimmune myositis, atherosclerosis, stroke, liver cirrhosis, meningitis, inflammatory gastric ulcer, gallbladder stone, kidney stone, paranasal sinusitis, rhinitis, conjunctivitis, asthma, dermatitis, inflammatory bowel disease, inflammatory collagen vascular disease, glomerulonephritis, inflammatory skin disease, rheumatoid arthritis, systemic lupus erythematosus, ankylosing spondylitis, Behcet's disease, ulcerative colitis, Crohn disease, psoriasis, atopic dermatitis, contact dermatitis, moist dermatitis, seborrheic dermatitis, lichen planus, lichen simplex chronicus, pemphigus, bellous pemphigus, epidermolysis bullosa, urticaria, angioedema, vasculitis, erythema, eosinophilia, nummular dermatitis, generalized exfoliative dermatitis, stasis dermatitis, disease of sebaceous gland, perioral dermatitis, pseudofolliculitus barbae, drug rash, erythema multiforme, erythema nodosum, granuloma annulare, or pelvic inflammatory disease (PID).

The inflammatory-induced bone disease may include a disease associated with bone, bone fracture, age-related bone loss, chondrodystrophy, hypercalcemia of malignancy, hyperostosis, osteopsathyrosis, osteomalacia, osteomyelitis, osteoporosis, Paget's disease, osteoarthritis, or rickets, but is not limited thereto.

In some embodiments, the non-cancerous cells of aberrant proliferation derived from inflammatory disease may include synovial cells of aberrant proliferation in a patient with rheumatoid arthritis.

The hyperproliferative vascular disorder may refer to a disorder caused by cells present in blood vessels, or in particular, by excessive proliferation of vascular smooth muscle cells.

The types of the non-cancerous cells of aberrant proliferation derived from the hyperproliferative vascular disorder are not particularly limited, but may be derived from vascular sclerosis, atherosclerosis, restenosis and stenosis, vascular malformation, vascular access stenosis associated with blood dialysis, transplant arteriopathy, vasculitis, vascular inflammatory disease, Digeorge syndrome, hereditary hemorrhagic telangeiectasia (HHT), keloid scar, blister disease, hyperproliferative vitreous syndrome, retinopathy of prematurity, myopic choroidal neovascularization, macular degeneration, diabetic retinopathy, neovascularization, primary pulmonary hypertension, asthma, nasal polyps, inflammatory bowel and periodontal disease, endometriosis, ovarian cysts, ovarian hyperstimulation syndrome, arthritis, rheumatoid arthritis, chronic articular rheumatism, synovitis, osteoarthritis, osteomyelitis, osteophytosis, septicemia, or vascular leak syndrome.

In some embodiments, the cells of aberrant proliferation derived from the inflammatory disease may include vascular endothelial cells of aberrant proliferation causing atherosclerosis, red blood cells of aberrant proliferation causing chronic myeloproliferative disorders, granulocytes, platelets, and lymphatic cells of aberrant proliferation known as angiofollicular lymphoid hyperplasia.

Genes that are inserted to the retroviral vector may be selected according to the purpose of experiments, but the types thereof are not limited thereto. The genes may include hormone, an enzyme, a carrier, or a gene expressing a drug for treating the cells of aberrant proliferation.

The composition of the present invention has a number of advantages as a carrier that delivers a foreign gene to aberrantly dividing cells of aberrant proliferation, such as cancer cells. The retrovirus is a non-lytic virus so that there will be no occurrence of cell lysis caused by virus release. In addition, an antibody specific to the non-lytic virus is not generated so that there will be no occurrence of viral clearance, and in this regard, the retrovirus is considered as an excellent gene carrier. The retrovirus can only infect dividing cells so that it specifically infects dividing cells of aberrant proliferation, such as cancer cells, and that is, it prevents a therapeutic gene from being expression in other normal cells. In this regard, the replication competent retrovirus can not only provide further stability to a cell curer, but also increase the efficiency of the gene delivery.

As shown in exemplary embodiments, when the infection rates of the vectors of the present invention are measured to confirm the gene delivery efficiency of the vectors, it is confirmed that, in the case of injecting the vector carrying the GaLV-Env gene into a transplanted brain tumor cell of a nude mouse, the vector had much greater influence than that of the vector carrying the MuLV-Env gene and was clearly proliferated in the entire cancerous tissues. In addition, it was confirmed that, at boundaries between the cancerous tissue and the normal cell, any of the normal cell was not infected with the virus. In this regard, it is deemed that the composition of the present invention is suitable for delivering genes targeting cells of aberrant proliferation, such as cancer cells.

The present invention provides a composition including a retrovirus for preventing or treating a disease causing aberrant proliferation of cells, wherein the retrovirus is produced by transfecting a cell strain.

The cells of aberrant proliferation may generally refer to the occurrence of inappropriately high levels of cell division by cell proliferation deviated from normal, suitable, or expected courses. In some embodiments, the cells of aberrant proliferation may include cells that have damaged or deleted DNA or other cellular components and that abnormally proliferate.

The disease causing the aberrant proliferation of cells may include cell proliferation with characteristics of a disease or a disorder that is caused by, mediated by, or resulted from the occurrence of cell division at inappropriately high levels. Such a disease or disorder may be, for example, a cancerous or non-cancerous disease or disorder, or a malignant or benign disease or disorder. The description thereof may be referred to that provided above.

In addition, the present invention provides a composition including the retrovirus for preventing or treating cancer, wherein the retrovirus is produced by transfecting a cell line with the vector system to which a foreign gene for cancer cells is inserted as a therapeutic gene for the cells of aberrant proliferation.

The first recombinant expression vector or the second recombinant expression vector provided in the present invention includes a therapeutic gene for cancer as the therapeutic gene of the cells of aberrant proliferation. The types of the therapeutic gene for cancer are not particularly limited, but may include at least one selected from the group consisting of an apoptosis-related gene, an apoptosis-inducing gene, an immune gene, an angiogenesis inhibitor gene, and a sequence that expresses shRNA, miRNA, or siRNA that induces gene silencing (RNAi) capable of killing cancer cells.

The type of the apoptosis-related gene is not particularly limited, but in some embodiments, the apoptosis-related gene may include thymidine kinase of herpes simplex virus or of bacteria or yeast cytosine deaminase gene.

The apoptosis-related gene may activate a prodrug. In some embodiments, when a prodrug is added to tumor cells after the apoptosis-related gene is introduced to the cells, the prodrug may be activated in respond to the apoptosis-related gene product.

The apoptosis-related genes may include herpes simplex virus thymidine kinase (HSV-TK), which may activate prodrug, GCV (Ganciclovir).

The HSV-TK may conduct phosphorylation of GCV 1,000 times more effectively than types of mammal thymidine kinase, and accordingly, the HSV-TK may increase the apoptosis effects of cancer cells.

The HSV-TK may convert the GCV (Ganciclovir) substrate, which is nucleoside analogs, to triphosphate in phosphorylation. Then, the phosphorylated GCV may be used in DNA synthesis of cells and may stop DNA replication. In this regard, the cell cycle arrest may occur, as well as apoptosis. In addition, the phosphorylated GCV may be delivered to a cell in which the TK gene is not expressed, through a gap junction of a cell in which the TK gene is expressed, thereby performing the same apoptosis effect.

As shown in exemplary embodiments, the HSV-TK gene is inserted to the vector of the present invention to test cell viability, and the results are as follows. Under conditions of GCV in concentrations of 10 μg/ml to 30 μg/ml, cytotoxicity is observed in a spRCR-TK infected U-87 MG cells without any damage found in a normal cell, and no virus is found in tissues other than the cancerous tissue. That is, it is confirmed that the composition of the present invention has good safety. In addition, as a result of an animal test, all mice in a control group die 40 days before and after performing cancer transplantation while all mice in a test group receiving everyday injections survive up to 70 days, which is the present point during the research after the cancer transplantation. In addition, it is confirmed that the mice in the test group maintain their normal weights.

Based on these results, it is confirmed that the composition of the present invention has high stability and is capable of delivering a therapeutic gene for cancer to dividing cancer cells in an efficient manner.

The existing anti-cancer treatment has been applied to the whole body as well as cancer cells, resulting in side effects. However, the apoptosis-related gene/prodrug system is capable of targeting cancer cells only, so that normal cells are not infected with prodrug. In addition, even if the vector fails to reach the target cells due to necrosis or hypoxia in a local area of a malignant tumor, the scope of the cancer therapy may be improved by bystander effect.

In manufacturing of a pharmaceutical composition including the retrovirus for preventing or treating cancer, wherein the composition is produced by transfecting a cell line with the vector system of the present invention, the content of the retrovirus may be in a range of about 0.01 wt % to about 99 wt % based on the total weights of the composition, but the range is not limited thereto.

The composition for preventing or treating cancer of the present invention may be prepared as a pharmaceutical composition by referring to the description provided in Remington's Pharmaceutical Science (latest edition; Mack Publishing Company, Easton Pa.). Here, examples of a pharmaceutically available carrier are lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talcum, magnesium stearate, and mineral oil, but are not limited thereto.

The composition of the present invention may include further include, in addition to the components above, a lubricant, a wetting agent, a sweetener, a flavoring agent, an emulsifier, a suspending agent, or a preservative.

The pharmaceutical composition may be administrated by various routes to mammals, such as rats, nice, cattle, and human. All the administration methods can be expected, but in some embodiments, the pharmaceutical composition may be administrated by injection into an oral, rectal or intravenous, muscle, subcutaneous, endobronchial inhalation, dura mater in the uterus, or intracerebroventricular region.

The composition of the present invention may have a suitable dosage that varies according to elements, such as a formulation method, administration means, a patient's age, weight, gender, and pathologic conditions, foods, administration time, excretion rate, and response sensitivity, and a skilled doctor may determine and prescribe suitable dosage for efficient treatment or prevention.

According to the methods that are obvious to one of ordinary skill in the art, the composition of the present invention may be formulated by using a pharmaceutically available carrier and/or diluting agent to be prepared in a unit capacity formation, or may be delivered into a high capacity container. Here, the formulation may include a solution in oil or aqueous medium, a suspension or an emulsion, an extract, powder, or a tablet or a capsule, and in addition, the composition may further include a dispersant or a stabilizer.

The present invention provides a method of manufacturing a pseudotyped replication-competent retrovirus vector system, the method including: preparing a first recombinant expression vector carrying the MuLV-Gag gene and the MuLV-Pol gene; and preparing a second recombinant expression vector carrying the GaLV-Env gene.

The types of the first recombinant expression vector are not particularly limited, but may have a vector having a plasmid map of FIG. 1.

The types of the second recombinant expression vector are not particularly limited, but may have a vector having a plasmid map FIG. 2.

The first recombinant expression vector or the second recombinant expression vector may insert a foreign gene targeting cancer cells, and the foreign gene may be a therapeutic gene for cancer.

An example of the vector including the therapeutic gene for cancer includes a vector having a plasmid map of FIG. 3.

Advantageous Effects

The vectors of the present invention, such as a first recombinant expression vector carrying the MuLV-Gag gene and the MuLV-Pol gene and a second recombinant expression vector carrying the GaLV-Env gene, wherein each of the genes targets cells of aberrant proliferation, a therapeutic gene may be inserted to both recombinant expression vectors, and in this regard, a variety of foreign genes for treatment may be inserted to the vectors without the size limitation of the insertional genes. The vectors may be infected at a high infection rate of about 94% to about 100% with aberrantly dividing cells of aberrant proliferation, such as cancer cells, to deliver foreign genes. Thus, the vectors are safe since the gene delivery does not specifically affect normal cells and the foreign genes may be delivered to parts where the only cells of aberrant proliferation exist. In some embodiments, in the case of using the vector of the present invention to which a therapeutic gene is inserted to the cells of aberrant proliferation, such as cancer cells, only cancer cells can be efficiently killed and accordingly, and all the testing subjects are remained alive until the end of the observing time in consideration of cell viability. Therefore, it is confirmed that the vector system of the present invention is efficient in preventing or treating disease causing the aberrant proliferation of cells, such as cancer cells, and accordingly, the vector system is considered applicable in a pharmaceutical composition for preventing or treating disease causing the aberrant proliferation of cells.

DESCRIPTION OF THE DRAWINGS

FIGS. 4 and 5 depict subcloning of a sRCRgp-RFP vector, wherein

FIG. 4 depicts that a pRCR(FvGEL199) vector is cut by ScaI and PmeI to remove a FvGEL199Env sequence and is self-ligated by a T4 DNA polymerase, and FIG. 5 depicts that an sRCRgp plasmid is cut by EcoRI to insert a marker gene, RFP, and is ligated with a fragment of mCMV promoter-RFP amplified by PCR from a pLentiM1.4-monomerRFP vector;

FIG. 6 depicts subcloning of a spRCRe(GaLV-Env)GFP vector, wherein FIG. 6A depicts that a pMFG-eGFP-Puro vector is cut by XhoI and ClaI to insert an mCMV promoter and a GFP sequence and is ligated with a fragment of mCMV promoter-RFP amplified by PCR from a pLentiM1.4-eGFP vector, and FIG. 6B depicts that a GaLV-Env sequence of a pMYK-ef1-GaLV-Env vector is amplified and inserted to a site that is cut by PmeI of the pMFG-mCMV-GFP2 vector (see FIG. 6A);

FIG. 7 depicts subcloning of a spRCRe(GaIV-Env)TK vector, wherein FIG. 7A depicts that, to perform subcloning of a spRCR (GaLV-Env)MCS vector, a spRCRe(GaLV-Env)-GFP vector is cut by a restriction enzyme to remove eGFP and is self-ligated and a multi-cloning site is inserted to the spRCR(GaLV-Env)MCS vector by PCR amplification. The spRCR(GaLV-Env)MCS vector is cut by PmeI to insert a TK sequence. FIG. 7B depicts that the TK fragment cut by PmeI from a pSXLC-TK vector is inserted to the spRCR(GaLV-Env)MCS vector;

FIG. 8 depicts a structure of a semi-pseudotyped replication-competent retrovirus (spRCR) vector that allows expression of a fluorescent marker protein, wherein FIG. 8A depicts the sRCRgp-RFP vector including two terminal LTRs, a structure for the Gag-Pol gene expression, and the RFP sequence, and the sRCRe(MuLV-Env)-GFP vector including an expression marker, a structure for the MuLV-Env gene expression, and the GFP sequence, and FIG. 8B depicts that the MuLV-Env gene of the sRCRe(MuLV-Env)-GFP vector is replaced by the GaLV-Env gene;

FIGS. 9 and 10 show replication kinetics of the sRCR (MuLV-Env)-FL and spRCR(GaLV-Env)-FL vectors with high titer, wherein FIGS. 9A and 9B show the results of measuring fluorescence by flow cytometry to determine percentages of cells that express a GFP gene or a RFP gene based on the observation of the cells under a fluorescence microscope at various time points after the cells were infected by $2.5 \times 10^7$ genomic copies of Human glioma cells (U-87 MG) with the sRCR-FL vector or the spRCR-FL vector;

FIG. 10 shows percentages of cells that express a GFP gene or a RFP gene measured by flow cytometry.

FIGS. 11 and 12 show replication kinetics of the sRCR (MuLV-Env)-FL and spRCR(GaLV-Env)-FL vectors with high titer, wherein FIGS. 11A and 11B show percentages of a GFP gene or a RFP gene expressed by an Env vector or a Gag-Pol vector, and FIG. 12 depicts a comparison between replication kinetics of a spRCRe(GaLV-Env)-GFP vector and that of a sRCRe(MuLV-Env)-GFP vector;

FIGS. 13 and 14 show replication kinetics of the sRCR (MuLV-Env)-FL and spRCR(GaLV-Env)-FL vectors with low titer, wherein FIGS. 13A and 13B show the results of measuring fluorescence by flow cytometry to determine percentages of cells that express a GFP gene or a RFP gene based on the observation of the cells under a fluorescence microscope at various time points after the cells were infected by $1.5 \times 10^6$ genomic copies of Human glioma cells (U-87 MG) with the sRCR-FL vector or the spRCR-FL vector;

FIGS. 15 and 16 show replication kinetics of the sRCR (MuLV-Env)-FL and spRCR(GaLV-Env)-FL vectors with low titer, wherein FIG. 15 shows percentages of a GFP gene or a RFP gene expressed by a Env vector and a Gag-Pol vector, and FIG. 16 depicts a comparison between replication kinetics of a spRCRe(GaLV-Env)-GFP vector and that of a sRCRe (MuLV-Env)-GFP vector;

FIGS. 19 and 20 depict cytotoxicity of a semi-RCR-TK/GCV vector in U-87 MG cells, wherein FIG. 19 depicts the results of the cell viability measured by MTT analysis by which spRCR(GaLV-Env)-TK transduced U-87 MG are treated with GCV in various concentrations from 0 to 70 µg/ml beginning at 0 day;

FIG. 20 depicts the results of the cell viability measured by MTT analysis by which spRCR(GaLV-Env)-FL, sRCR (MuLV-Env)-TK, and spRCR(GaLV-Env)-TK transduced U-87 MG cells are treated with GCV in a concentration of 10 µg/ml;

FIG. 21 depicts dispersion of a semi-RCR virus in human gliomas, wherein FIG. 21A depicts that human glioma (U-87 MG) are infected with a striatum of a nude mouse to form cancer cells, and after 7 days of the infection, $1.5 \times 10^7$ genomic copies ($10^4$ TU) of a semi-RCR-FL vector are injected to the heterotransplanted cancer cells, and after 18 days of the viral infection, the cancer cells are subjected to cryosection. FIGS. 21B and 21C are integrated images showing the expression of the GFP gene or the RFP gene by the dispersion of the sRCR(MuLV-Env)-FL vector (FIG. 21B) or the spRCR(GaLV-Env)-FL vector (FIG. 21C);

BEST MODE

The present invention provides including a first recombinant expression vector carrying a MuLV-Gag gene and a MuLV-Pol gene; and a second recombinant expression vector carrying a GaLV-Env gene.

Figure 1:
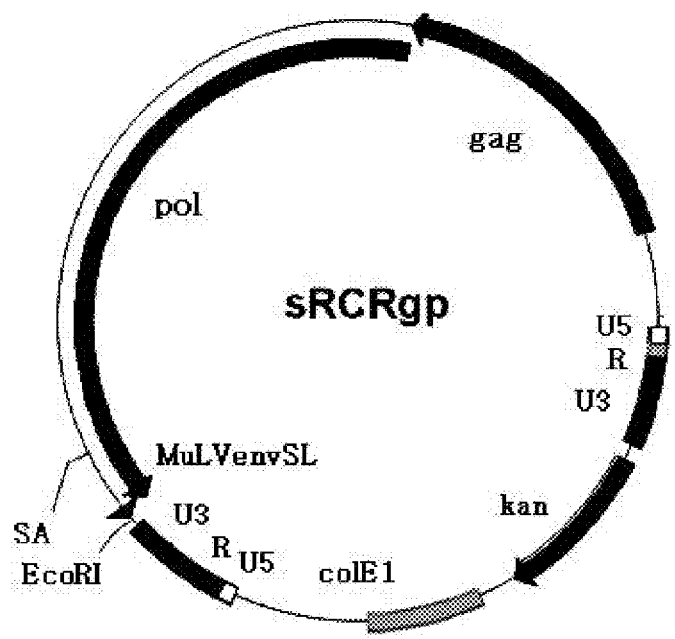
FIG. 1 is a plasmid map of a first recombinant expression vector carrying a gag gene and a pol gene.

The first recombinant expression vector may include a vector having a plasmid map of FIG. 1.

Figure 2:
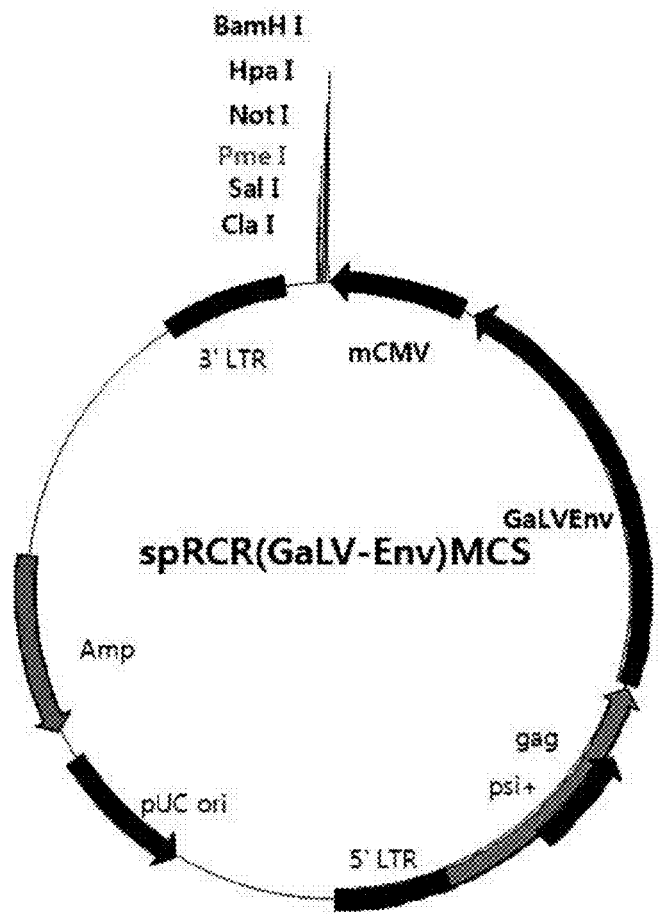
FIG. 2 is a plasmid map of a second recombinant expression vector carrying a GaLV-Env gene.

The second recombinant expression vector may include a vector having a plasmid map of FIG. 2.

The first recombinant expression vector of the second recombinant expression vector may include a therapeutic gene for cells of aberrant proliferation.

Figure 3:
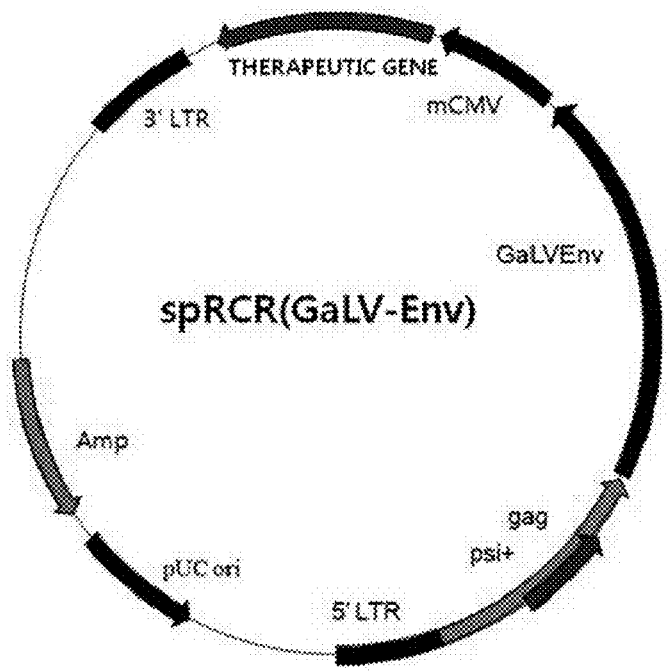
FIG. 3 depicts the second recombinant expression vector to which a therapeutic gene is added.

The second recombinant expression vector may include a vector having a plasmid map of FIG. 3.

The present invention provides a retrovirus produced by transfecting a cell strain with the vector system.

The present invention provides a composition including the retrovirus for delivering genes targeting cells of aberrant proliferation.

The cells of aberrant proliferation may be cancer cells.

The cancer cells may include cells derived from myxoid and round cell carcinomas, locally advanced tumors, metastatic cancer, Ewing's sarcoma, cancer metastasis, lymphatic metastasis, squamous epithelial cell carcinoma, esophagus squamous epithelial cell carcinoma, oral carcinoma, multiple myeloma, acute lymphocytic leukemia, acute non-lymphocytic leukemia, chronic lymphocytic leukemia, chronic myelocytic leukemia, hairy cell leukemia, effusion lymphoma (body cavity based lymphoma), thymic lymphoma lung cancer, small cell carcinoma of the lung, cutaneous T-cell lymphoma, Hodgkin's lymphoma, non-Hodgkin's lymphoma, cancer of the adrenal cortex, ACTH-producing tumor, non-small cell carcinoma of the lung, breast cancer, small cell carcinoma, ductal carcinoma, stomach cancer, colon cancer, colorectal cancer, polyp associated with colorectal neoplasia, pancreatic cancer, liver cancer, bladder cancer, primary superficial bladder tumor, invasive transitional cell carcinomas of the bladder, muscle-invasive bladder cancer, prostate cancer, renal cell carcinoma, esophagus cancer, ovarian carcinoma, uterine cervical cancer, endometrial cancer, choriocarcinoma, ovarian cancer, primary peritoneal epithelial neoplasm, cervical carcinomas, vaginal cancer, cancer of the vulva, uterine cancer, solid tumor in the ovarian follicle, testicular cancer, penile cancer, renal cell carcinoma, brain cancer, head and neck cancer, neuroblastoma, asfrocytic brain tumor, glioma, metastatic tumor cell invasion in the central nervous system, osteoma, osteosarcoma, malignant melanoma, tumor progression of human skin keratinocyte, thyroid cancer, retinoblastoma, neuroblastoma, mesothelioma, Wilms's tumor, gall bladder cancer, trophoblastic neoplasm, hemangiopericytoma, or Kaposi's sarcoma.

The cells of aberrant proliferation may be non-cancer cells derived from inflammatory disease or hyperproliferative vascular disorder.

The non-cancerous cells of aberrant proliferation derived from the inflammatory disease may include cells derived from inflammatory-induced bone disease, degenerative arthritis, diabetes, autoimmune myositis, atherosclerosis, stroke, liver cirrhosis, meningitis, inflammatory gastric ulcer, gallbladder stone, kidney stone, paranasal sinusitis, rhinitis, conjunctivitis, asthma, dermatitis, inflammatory bowel disease, inflammatory collagen vascular disease, glomerulonephritis, inflammatory skin disease, rheumatoid arthritis, systemic lupus erythematosus, ankylosing spondylitis, Behcet's disease, ulcerative colitis, Crohn disease, psoriasi, atopic dermatitis, contact dermatitis, moist dermatitis, seborrheic dermatitis, lichen planus, lichen simplex chronicus, pemphigus, bellous pemphigus, epidermolysis bullosa, urticaria, angioedema, vasculitis, erythema, eosinophilia, nummular dermatitis, generalized exfoliative dermatitis, stasis dermatitis, disease of sebaceous gland, perioral dermatitis, pseudofolliculitus barbae, drug rash, erythema multiforme, erythema nodosum, granuloma annulare, or pelvic inflammatory disease (PID).

The non-cancerous cells of aberrant proliferation derived from the hyperproliferative vascular disorder may include cells derived from vascular sclerosis, atherosclerosis, restenosis and stenosis, vascular malformation, vascular access stenosis associated with blood dialysis, transplant arteriopathy, vasculitis, vascular inflammatory disease, Digeorge syndrome, hereditary hemorrhagic telangeiectasia (HHT), keloid scar, blister disease, hyperproliferative vitreous syndrome, retinopathy of prematurity, myopic choroidal neovascularization, macular degeneration, diabetic retinopathy, neovascularization, primary pulmonary hypertension, asthma, nasal polyps, inflammatory bowel and periodontal disease, endometriosis, ovarian cysts, ovarian hyperstimulation syndrome, arthritis, rheumatoid arthritis, chronic articular rheumatism, synovitis, osteoarthritis, osteomyelitis, osteophytosis, septicemia, or vascular leak syndrome.

The present invention provides a composition including a retrovirus for preventing or treating a disease causing aberrant proliferation of cells, wherein the retrovirus is produced by transfecting a cell strain.

The therapeutic gene for cancer may include at least one selected from the group consisting of an apoptosis-related gene, an apoptosis-inducing gene, an immune gene, an angiogenesis inhibitor gene, and a sequence that expresses shRNA, miRNA, or siRNA that induces gene silencing (RNAi) capable of killing cancer cells.

The apoptosis-related gene may activate a prodrug.

The apoptosis-related genes may include herpes simplex virus thymidine kinase (HSV-TK), which may activate prodrug, GCV (Ganciclovir).

The present invention provides a method of manufacturing a pseudo-type replication-competent retrovirus vector system, the method including: preparing a first recombinant expression vector carrying the MuLV-Gag gene and the MuLV-Pol gene; and preparing a second recombinant expression vector carrying the GaLV-Env gene.

MODE OF THE INVENTION

The present invention provides a vector system in which a MuLV-Gag gene, a MuLV-Pol gene, and a GaLV-Env gene are expressed in two separate vectors, a retrovirus produced by transfecting a cell strain with the vector system, a composition including the retrovirus for delivering genes targeting cells of aberrant proliferation, a composition for preventing and treating cancer, and a method of manufacturing the vector system in which the MuLV-Gag gene, the MuLV-Pol gene, and the GaLV-Env gene are expressed in two separate vectors. The present invention will now be described in greater detail with reference to the following examples. In this regard, the present Examples are merely described to explain aspects of the present description and should not be construed as being limited to the descriptions set forth herein.

EXAMPLE

Example 1

Cell Culture 293T (human embryonic kidney) cells and U-87 MG (human glioma) cells were cultured in Dulbecco's Minimal Essential Medium (DMEM, Thermo Hyclone) to which 10% fetal bovine serum (Invitrogen) and antibiotics (Invitrogen) were added. In all experiments, cells were cultured in a cell culture vessel (e.g., a 100 mm dish and a 6-well plate) in a 5% $CO_2$ incubator, and then, were subjected to subcloning at a ratio of 1:5 when the frequency of the cultured cells reached 70% to 80%.

Example 2

Manufacture of Vector

Figure 4:
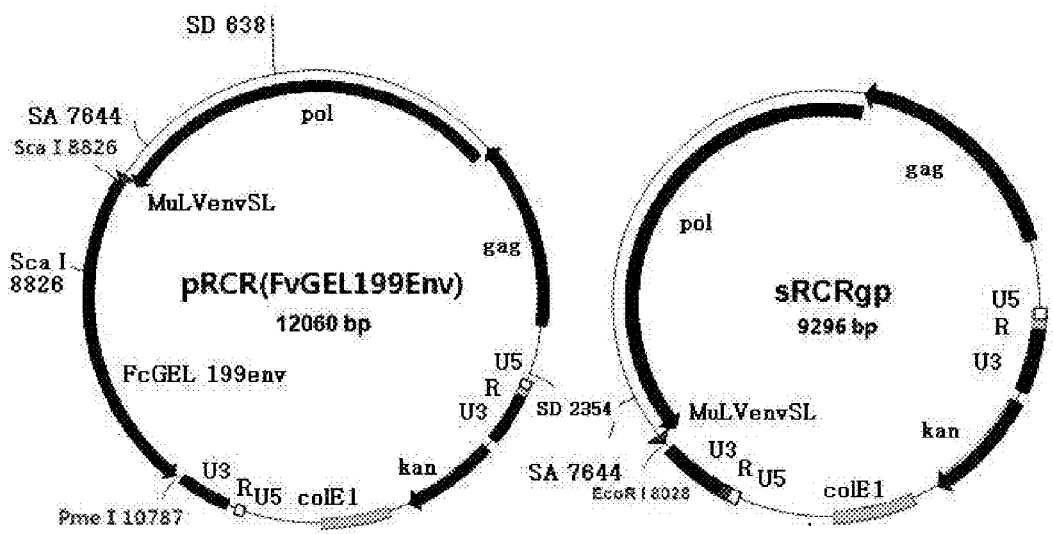
Figure 5:
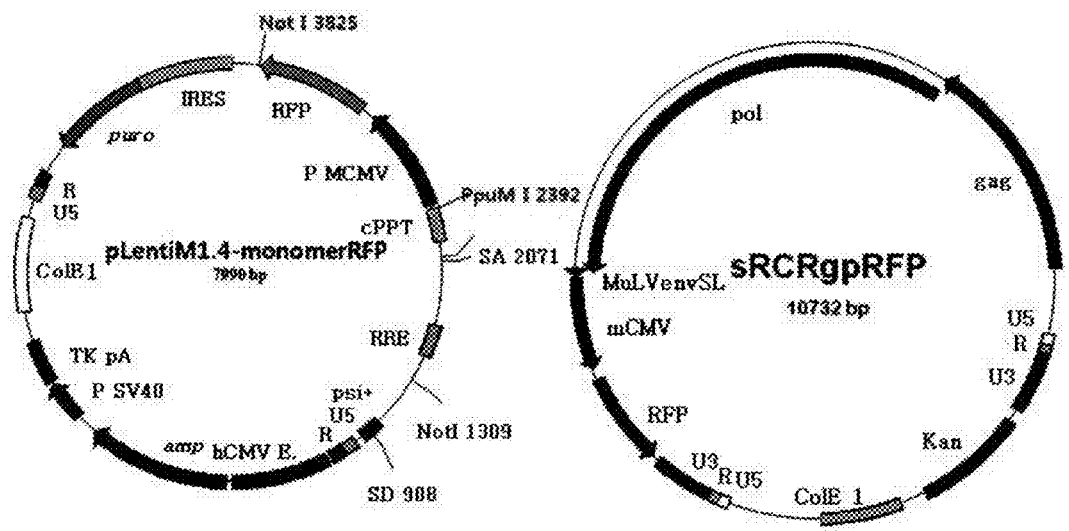

In order to manufacture a sRCRgp-RFP vector carrying a marker gene, RFP (see FIGS. 4 and 5), a FvGel199Env gene of a pRCR (FvGEL199Env) vector was cut and removed by Sca I and Pme I. Genes from an mCMV promoter to a RFP gene of a pLenti M1.4-momomerRFP vector were cut by PpuM I and Not I, thereby connecting the genes to the pRCR (FvGEL199Env) vector by blunt end ligation.

Figure 6:
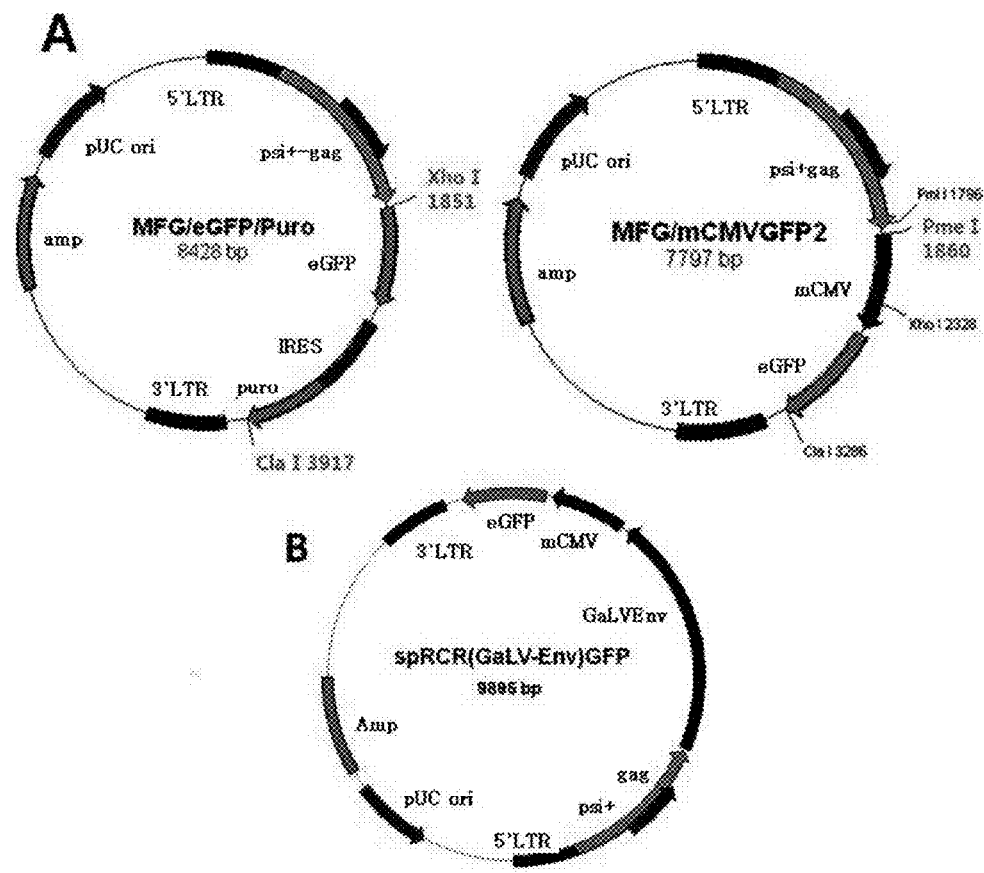

In order to manufacture a spRCRe (GaLV-Env)-GFP vector carrying a marker gene, GFP (see FIG. 6), an Xho I site in downstream of a gag gene and a Cla I site in upstream of 3'LTR of a MFG-eGFP-Puro vector were cut and removed. Genes from an mCMV gene to an eGFP gene, which were cut from a pLenti M1.4-eGFP vector, were amplified by PCR for ligation, thereby manufacturing a MFG-mCMV-GFP2 vector (Forward: Sal I-Pme I-mCMV, Reverse: Cla I-GFP). In order to insert a GaLV-Env sequence to a site between the Gag gene and the mCMV gene of the MFG-mCMV-GFP2 vector, PCR was performed by using a MYK-ef1-GaLV-Env vector as a template and a primer set each including a Pme I site. Then, the previously manufactured vector was cut by Pme I to ligate with an insert.

In order to insert a therapeutic gene instead of a marker gene, an eGFP gene was cut by BamH I and Cla I, and then, inserted to a multi cloning site, thereby manufacturing a spRCR (GaLV-Env)-MCS vector.

Figure 7:
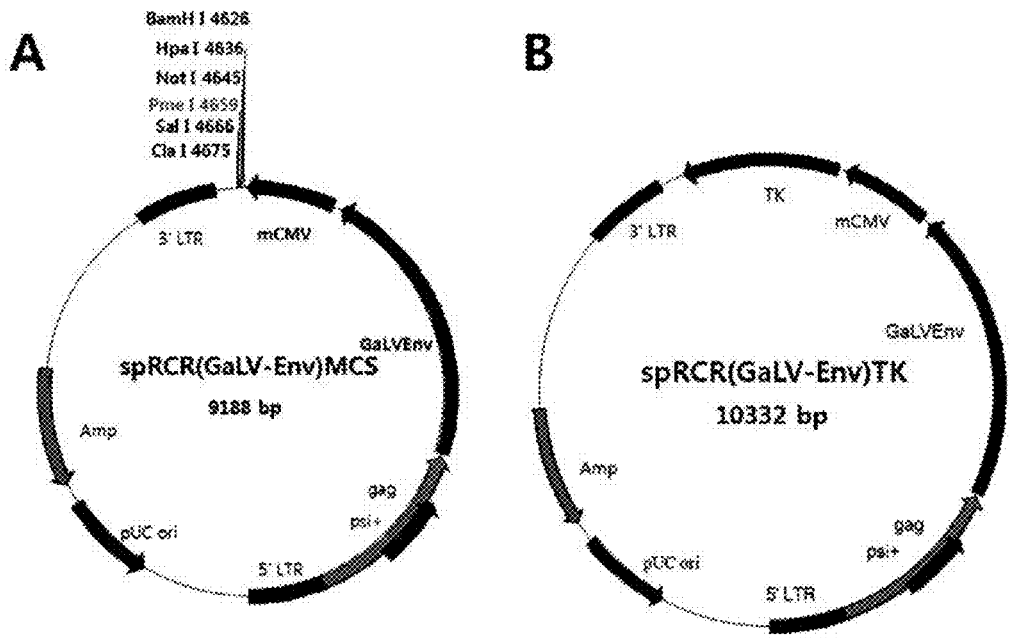

In order to insert a TK gene to the spRCR (GaLV-Env)-MCS vector (see FIG. 7), a pSXLC-TK vector was cut by Nco I and Xho I and was resulted in blunt ends by a T4 DNA polymerase (TAKARA). Afterwards, the spRCR(GaLV-Env)-MCS vector was cut by Pme I, followed by being treated with CIAP and ligated with an insert.

In order to manufacture a sRCRe (MuLV-Env) vector, a site in upstream of the mCMV was cut by Pme I from the previously manufactured MFG-mCMV-GFP2 vector. In order to prepare an Amphotropic MuLV-Env insert, a MuLV-Env gene of an EQPAM-Am vector was subjected to PCR for ligation using a primer set each including a Pml I location in forward and reverse sites.

In order to insert a TK gene to the sRCR (MuLV-Env)-RFP vector, both ends of a RFP gene were cut by Hpa I from the sRCR (MuLV-Env)-RFP vector, and the TK gene was cut by Hpa I and Cla I from a spRCR (GaLV-Env)-TK vector and was resulted in blunt end ligation.

TABLE 1

| Vector | Fragment | Ligation step |
|---|---|---|
| sRCRgp-RFP | Vector | pRCR(FvGEL199Env)→ Sca I, Pme I → self ligation (sRCRgp) → EcoR I → T4DNAPol → CIAP |
| | Insert | pLentiM1.4-monomerRFP → PpuM I, Not I→ T4DNAPol |
| | Ligation | Blunt end ligation |

TABLE 2

| Vector | Fragment | Ligation step |
|---|---|---|
| spRCRe (GaLV-Env)-GFP | Vector1 | MFG-eGFP-Puro → Xho I, Cla I → T4 DNA Pol → CIAP |
| | Insert1 | M1.4-eGFP → PCR Forward(Sal I-Pme I-mCMV): CC GTCGAC GTTTAAAC AACAGGAAAGTTCCATTG Reverse(Cla I-GFP): CC ATCGAT TTACTTGTACAGCTCGTCCA |
| | Ligation1 | Blunt end ligation (MFG-mCMV-GFP2) |
| | Vector2 | MFG-mCMV-GFP2 → Pme I → CIAP |
| | Insert2 | MYK-ef1-GaLV EnV → PCR Forward(Pml I-GaLV-Env): CGG CACGTG ATGGTATTGCTGCCTGGG Reverse(GaLV-PmlI-R): GCC CACGTG TTAAAGGTTACCTTCGTT → Pml I cut |
| | Ligation2 | Sticky end ligation |
| spRCR(GaLV-Env)-TK | Vector1 | spRCR(GaLV-Env)-GFP → BamH I, Cla I → cutting out |
| | Insert1 | PCR(Multi cloning site) Forward(BamH I, Hpa I, Not I, Pme I, Sal I, Cla I): CG GGATCC GC GTTAAC ATTT GCGGCCGC TTTA GTTTAAAC GC GTCGAC |

TABLE 2-continued

| Vector | Fragment | Ligation step |
|---|---|---|
| | | CC ATCGAT GG<br>Reverse(BamH I, Hpa I, Not I,<br>Pme I, Sal I, Cla I):<br>CC ATCGAT GG GTCGAC GC GTTTAAAC<br>TAAA GCGGCCGC AAAT GTTAAC GC<br>GGATCC CG →<br>BamH I, Cla I cut |
| | Ligation1 | Sticky end ligation |
| | Vector2 | spRCRe(GaLV-Evn)-MCS → Pme I cut |
| | Insert2 | pSXLC-TK → Nco I, Xho I → T4 DNA Pol |
| | Ligation2 | Blunt end ligation |

TABLE 3

| Vector | Fragments | Ligation step |
|---|---|---|
| sRCR(MuLV-Env)-GFP | Vector | MFG-mCMV-GFP2 → Pml I, Pme I → CIAP |
| | Insert | EQPAM-Am(AF010170) → PCR<br>Forward(Pml I-MuLV-Env):<br>CGG CACGTG<br>ATGGCGCGTTCAACGCTCTCA<br>Reverse(Pml I-MuLV-Env):<br>GCC CACGTG<br>CTATGGCTCGTACTCTATAGG →<br>Pml I cut |
| | Ligation | Blunt end ligation |
| sRCR(MuLV-Env)-TK | Vector1 | MFG-mCMV-GFP2 → BamH I, Cla I |
| | Insert1 | shLenti2.4R → PCR<br>Forward(BamH I-Hpa I-RFP):<br>CG GGATCC<br>GTTAACATGGCCTCCTCCGAGAACGTC<br>Reverse(Hpa I-Cla I-RFP):<br>CC ATCGAT GTTAAC<br>CTACAGGAACAGGTGGTGGCG →<br>BamH I, Cla I cut |
| | Ligation1 | Sticky end ligation (MFG-mCMV-RFP) |
| | Vector2 | MFG-mCMV-RFP → Pml I → CIAP |
| | Insert2 | pGEM-T-EQPAMEnv#2 → Pml I |
| | Ligation2 | Blunt end ligation (sRCR(MuLV-Env)-RFP) |
| | Vector3 | sRCR(MuLV-Env)-RFP → Hpa I cutting out → CIAP |
| | Insert3 | spRCR(GaLV-Env)-TK → Hpa I, Cla I cut → T4 DNA Pol |
| | Ligation3 | Blunt end ligation |

Example 3

Virus Production

One day before performing transfection, 293T cells were inoculated with a growth medium at $6 \times 10^5$ cells/well in a 6-well plate. Next day, 1 ml of the growth medium was replaced by an FBS-free DMEM medium. The 6-well plate was placed again in an incubator, and 100 μl/well of a DMEM medium was added to two separate 1.5 ml tubes. DNA (total 1 μg) of Tables above and PLUS reagent (Invitrogen) (5 μl/well) were added to one tube while lipopectamine reagent (Invitrogen) (3 μl/well) was added to another tube, and each of which tubes was vortexed for 10 seconds. After culturing at room temperature for 15 minutes, a solution from the lipopectamine-containing tube was added to the PLUS-containing tube, and then, the PLUS-containing tube was vortexed again for 10 seconds. After culturing at room temperature for 20 minutes, the plate where the cells underlay at the bottom of the plate was taken out from the incubator, and 208 μl/well of the cells was added dropwise without losing the cells to the tube. After placing the tube back to the incubator, the cell medium was removed in 4 hours and a DMEM media containing 3% FBS were added carefully thereto. Here, viruses to be used in animal experiments did not contain FBS. 48 hours later, the cell medium was harvested and collected in a tube. For the concentration and purification of the cells, the viruses were added to Amicon 100K (Millipore) and centrifuged at a temperature of 4° C. at 3,000 rpm until the number of the viruses reached 10× greater. The resultant included in the 1.5 ml tube was labeled with a date that the tube was prepared, and was divided by 100 μl and stored at a temperature of −80° C.

In order to quantitate the virus, a Retrovirus Titer Set for Realtime PCR (TaKaRa) was used. The kit includes a primer that recognizes a packaging signal region of MuLV, and a marker probe, SYBR Green I. An excess of DNA was used during the virus transfection. Thus, in order to remove such an excess of DNA, DNase I process [25 μl in total (Virus Supernatant 12.5 μl, 10×DNase Buffer 2.5 μl, DNase(5 U/μl) 2.0 μl RNase Inhibitor (40 μl) 0.5 μl, RNase-Free Water 7.5 μl); 37° C., 30 min/70° C., 1 minute] was performed thereafter.

A standard sample was prepared by serial dilution with RNA control template included in the Kit. The real time PCR was performed as follows (103, 104, 105, 106, 107, 108 copies/μl) [25 μl in total (2× One Step SYBR RT-PCR Buffer III 12.5 μl, TaKara Ex Taq HS (5 u/μl) 0.5 μl, PrimeScript RT Enzyme Mix II 0.5 μl, Forwaard Titer Primer FRT-1 (10 pmol/μl) 0.5 μl, Reverse Titer Primer FRT-1 (10 pmol/μl) 0.5 μl, 2 μl of a virus supernatant or a standard sample, 8.5 μl of RNase-Free Water; Reverse transcription, 42° C., 5 minutes/ 95° C., 10 seconds; PCR, 40 cycles, 95° C., 5 seconds/60° C. 30 seconds; Dissociation, 95° C., 15 seconds/60° C., 30 seconds/95° C., 15 seconds].

A standard curve was drawn and a sample value was calculated therefrom.

TABLE 4

| Transfer gene | Vector | Vector used in virus production |
|---|---|---|
| Reporter gene | sRCR-FL | sRCRgp-RFP + sRCRe(MuLV-env)-GFP |
| | spRCR-FL | sRCRgp-RFP + spRCRe(GaLV-env)-GFP |
| Therapeutic gene | sRCR-TK | sRCRgp-RFP + sRCRe(MuLV-env)-TK |
| | spRCR-TK | sRCRgp-RFP + spRCRe(GaLV-env)-TK |

Example 4

Replication Patterns According to Times Required for spRCR Vector In Vitro

Figure 8:
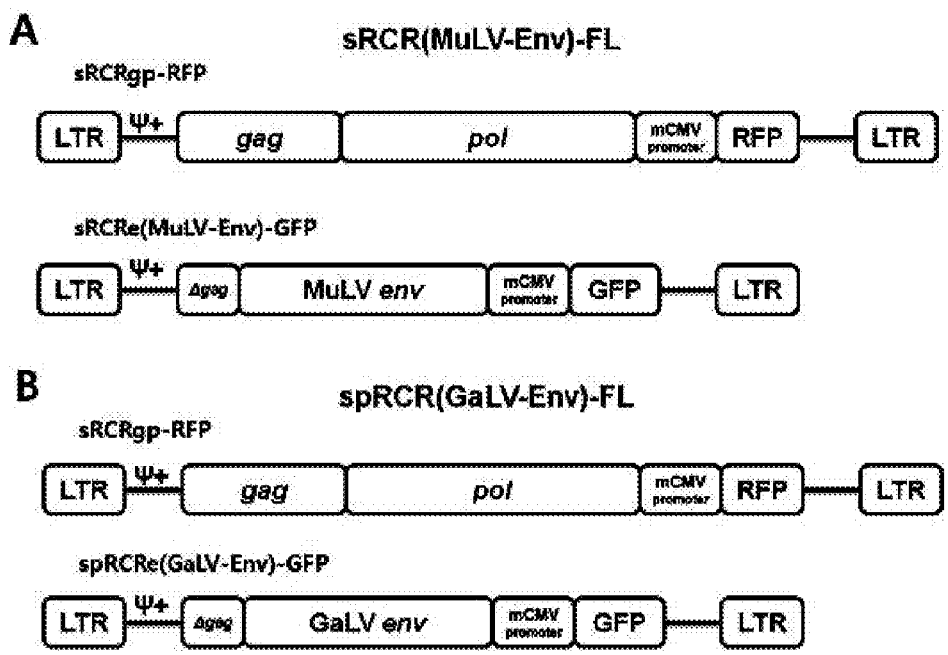
Figure 11:
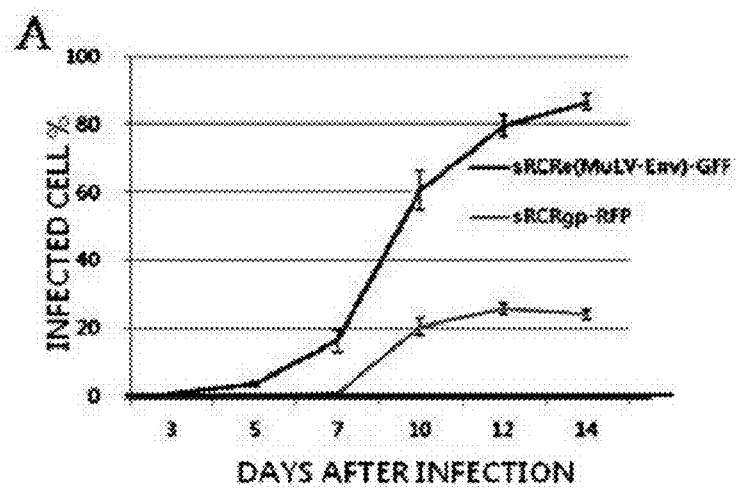
Figure 12:
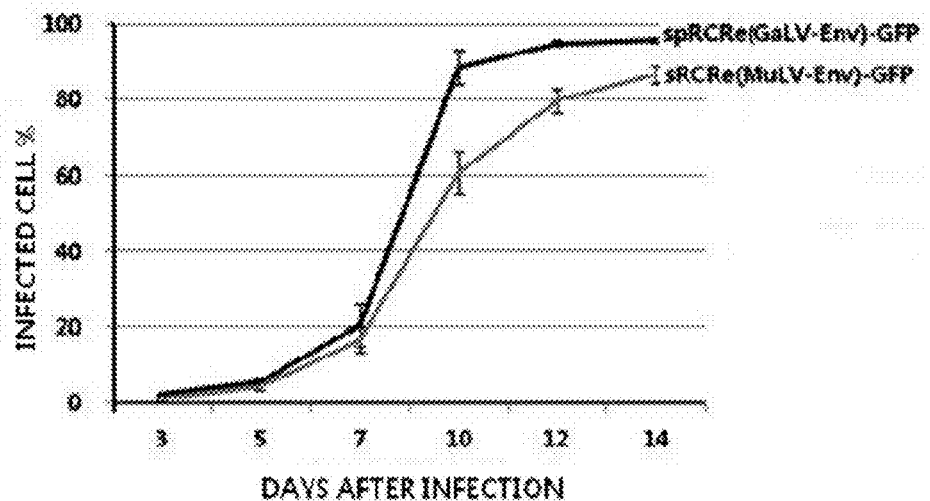
Figures 13, 14:
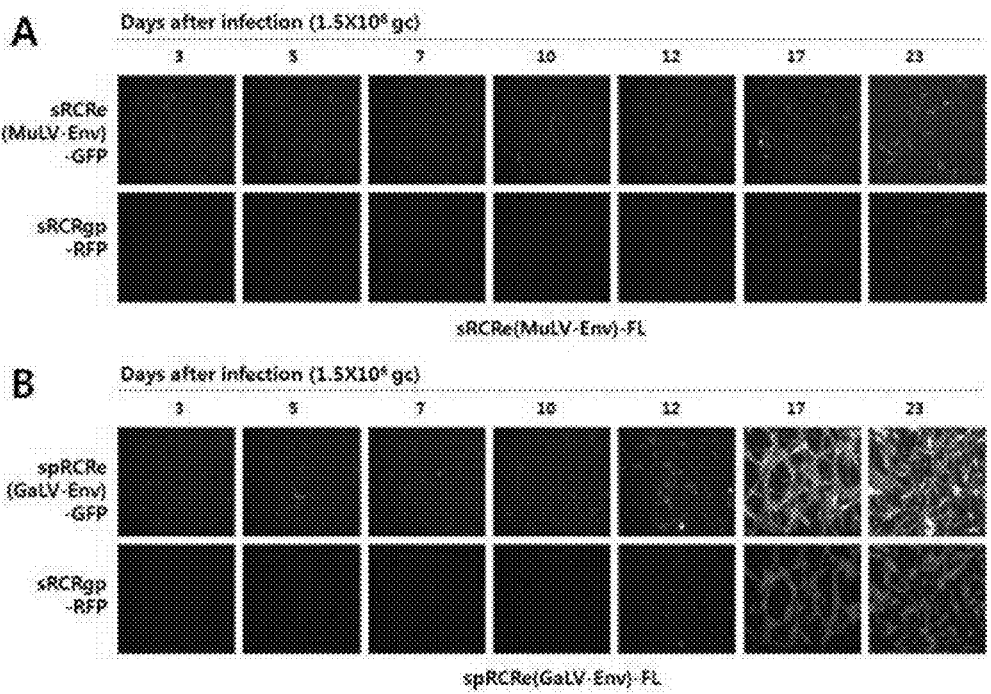

A conventional RCR vector associated with MuLV virus allowed expression of Gag-Pol, MuLV-Env, and a reporter gene (or a therapeutic gene) in one vector. However, the semi-pseudotyped replication-competent retrovirus (spRCR) vector as used herein allowed expression of Gag-Pol, GaLV-Env, and a reporter gene (or a therapeutic gene) in two separate vectors. Thus, a sRCRgp vector allowed expression of Gag-Pol, and its intracellular expression may be confirmed by RFP. The sRCRe(MuLV-Env) and the spRCRe(GaLV-Env) vectors each allowed the expression of MuLV-Env and GaLV-Env, which may be confirmed by GFP (FIG. 8).

The virus was produced through a top agar medium by transient transfection of the 293T cells with the two separate vectors. The same virus was subjected to quantitative real time PCR to calculate the number of genomic copies. $2.5 \times 10^7$ and $1.5 \times 10^6$ genome copies (gc) (0.01MOI, 0.0005MOI) of spRCR-FL and sRCR-FL were each infected with U-87 MG cells, and every 2 to 3 days, a fluorescence image of the cells was obtained before carrying out the subcloning. The cells remained after the subculturing were then subjected to FACS analysis. According to FACS data, in the case of the cell infection with high titer (genome copy, gc), the infection rate or fluorescence intensity of the spRCR (GaLV-Env) was relatively higher than that of the sRCR (MuLV-Env). After 12 days of the infection, the sRCR (MuLV-Env) vector was remained at 80% infection yet while the spRCR(GaLV-Env) vector was close to 100% infection (see FIGS. 9 to 12). Alternatively, in the case of the cell infection with low titer, the spRCR(GaLV-Env) and sRCR(MuLV-Env) vectors had a more obvious difference in infection rates therebetween. These two vectors had slow infection rates at the beginning of the infection in the case of the cell infection with low titer, but 20 days after the cell infection, the sRCR(MuLV-Env) vector was resulted in only 2% infection while the spRCR(GaLV-Env) vector was resulted in 94% infection (see FIGS. 13 to 16).

Example 5

Confirmation of Thymidine Kinase Protein Expressed in spRCR-TK

Figure 17:
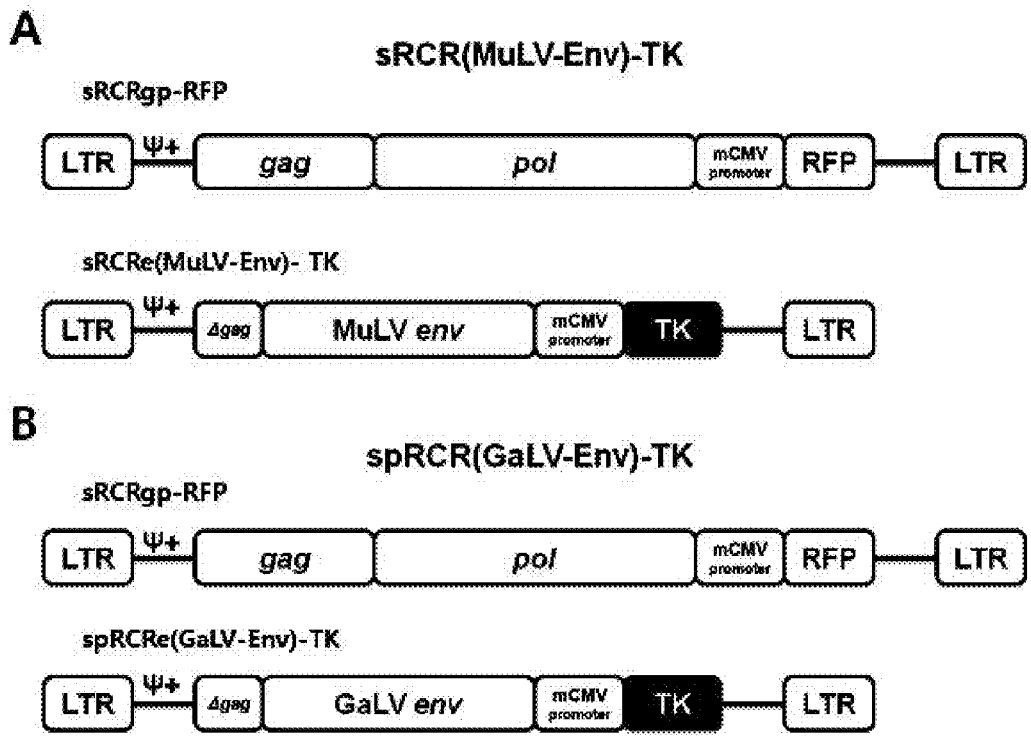
FIG. 17 depicts a structure of a spRCR vector that allows gene expression, wherein FIGS. 17A and 17B each depicts a structure of an Env vector in which a GFP gene is replaced by herpes simplex virus type I thymidine kinase (TK) gene.

A GFP gene was deleted from an Env vector that allows expression of a reporter gene, and then, a therapeutic gene, thymidine kinase (TK) was cloned thereto (see FIG. 17). In order to confirm whether the TK protein is actually expressed in the spRCR-TK vector, a western blotting was performed.

Figure 18:
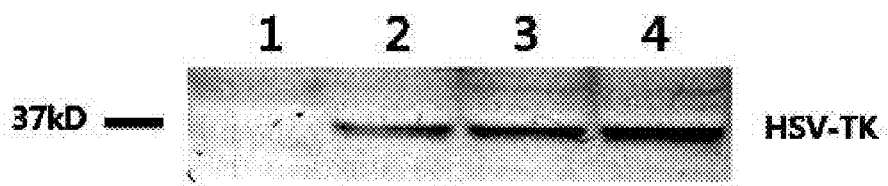
FIG. 18 depicts the expression of the TK gene of the spRCR vector that allows expression of the TK gene, based on the observation of the HSV-TK expression in A549 cells by a western blotting, wherein Lane 1 denotes untreated A549 cells, Lane 2 denotes A549 cells infected with a spRCR(GaLV-Env)-TK virus, and Lane 3 denotes A549 cells infected with a sRCR(MuLV-Env)-TK virus, and Lane 4 denotes gp293 cells transfected with a spRCR(GaLV-Env)-TK plasmid.

As shown in FIG. 18, it was confirmed that no band appeared in untreated A549 cells while bands appeared in cells that were infected or transduced with spRCR-TK, sRCR-TK, and pRCR-TK, which allow expression of the TK gene.

Example 6

Sensitivity of Cells Infected with spRCR-TK Vector According to GCV Concentrations In order to measure a degree of cytotoxicity of the cells infected with the spRCR-TK vector when treated with GCV in vitro, MTT assay was carried out. First, a vector carrying a therapeutic gene, TK, instead of a GFP gene of the Env vector was prepared. Then, the 293T cells were transfected with the prepared vector and a Gag-pol vector, so as to manufacture the spRCR-TK vector. Then, the U-87 MG cells were infected with the virus of the spRCR-TK vector, and maintained for 14 days. Afterwards, the infected cells and non-infected cells were inoculated into a 96-well plate. Next day after the inoculation, the concentration of GCV was gradually increased to 0, 10, 20, 30, 40, 50, 60, and 70 μg/ml for the treatment. The GCV treatment period was divided as the $1^{st}$, $2^{nd}$, $3^{rd}$, and $4^{th}$ day, to perform MTT assay.

Figure 19:
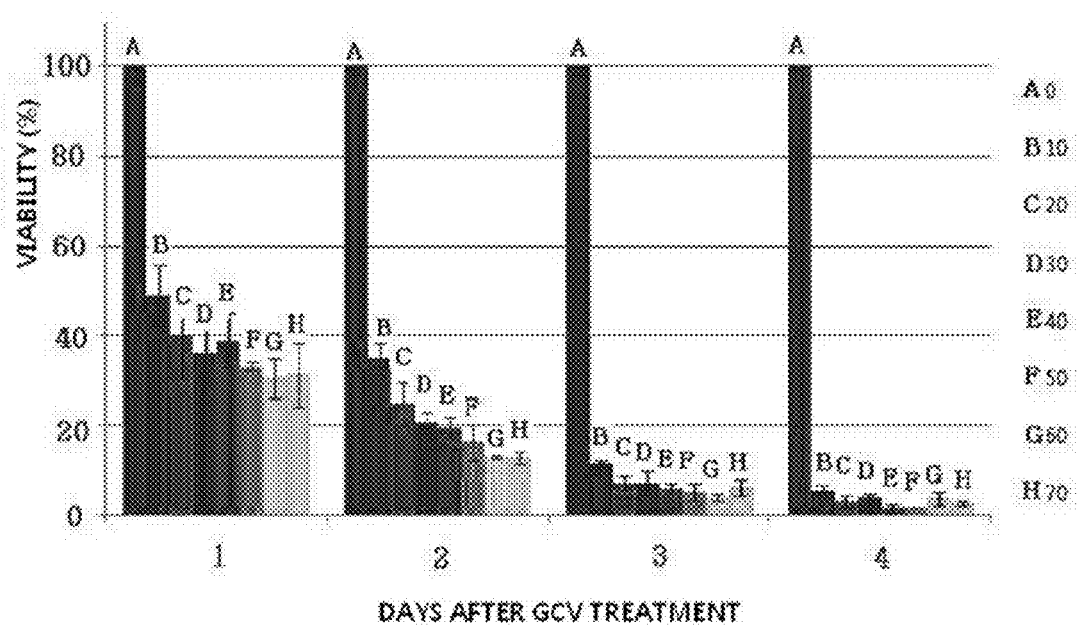
Figure 20:
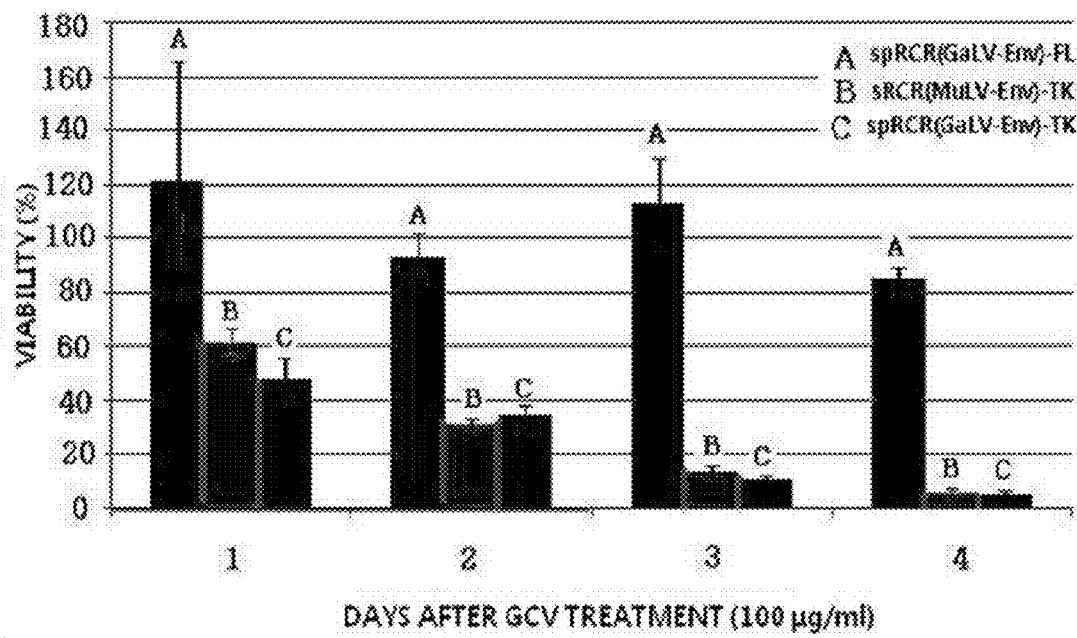

In the $1^{st}$ day of the treatment with 10 μg/ml of GCV, the number of the cells infected with the sRCR-TK vector was decreased by 40% one day after the GCV treatment, and the number of the cells infected with the spRCR-TK vector was decreased by 60%. Meanwhile, normal cells showed their cytotoxicity in concentration starting from GCV 70 μg/ml (see FIGS. 19 and 20).

Example 7

Spread Pattern of spRCR-FL and sRCR-FL Vectors in Xenografted Tumor Tissues

In order to figure out spread pattern of the spRCR-FL and sRCR-FL vectors in xenografted tumor tissue of a nude mouse, a brain striatum of the nude mouse was transplanted with $3 \times 10^5$ of the U-87 MG cells. After 7 days of the cancer transplantation, $1.5 \times 10^7$ gc ($\approx 10^4$ TU)/10 μl of a viral vector was injected to the tumor tissue. After 18 days of the viral injection, the tumor tissue was examined by using a fluorescent microscope.

Figure 21:
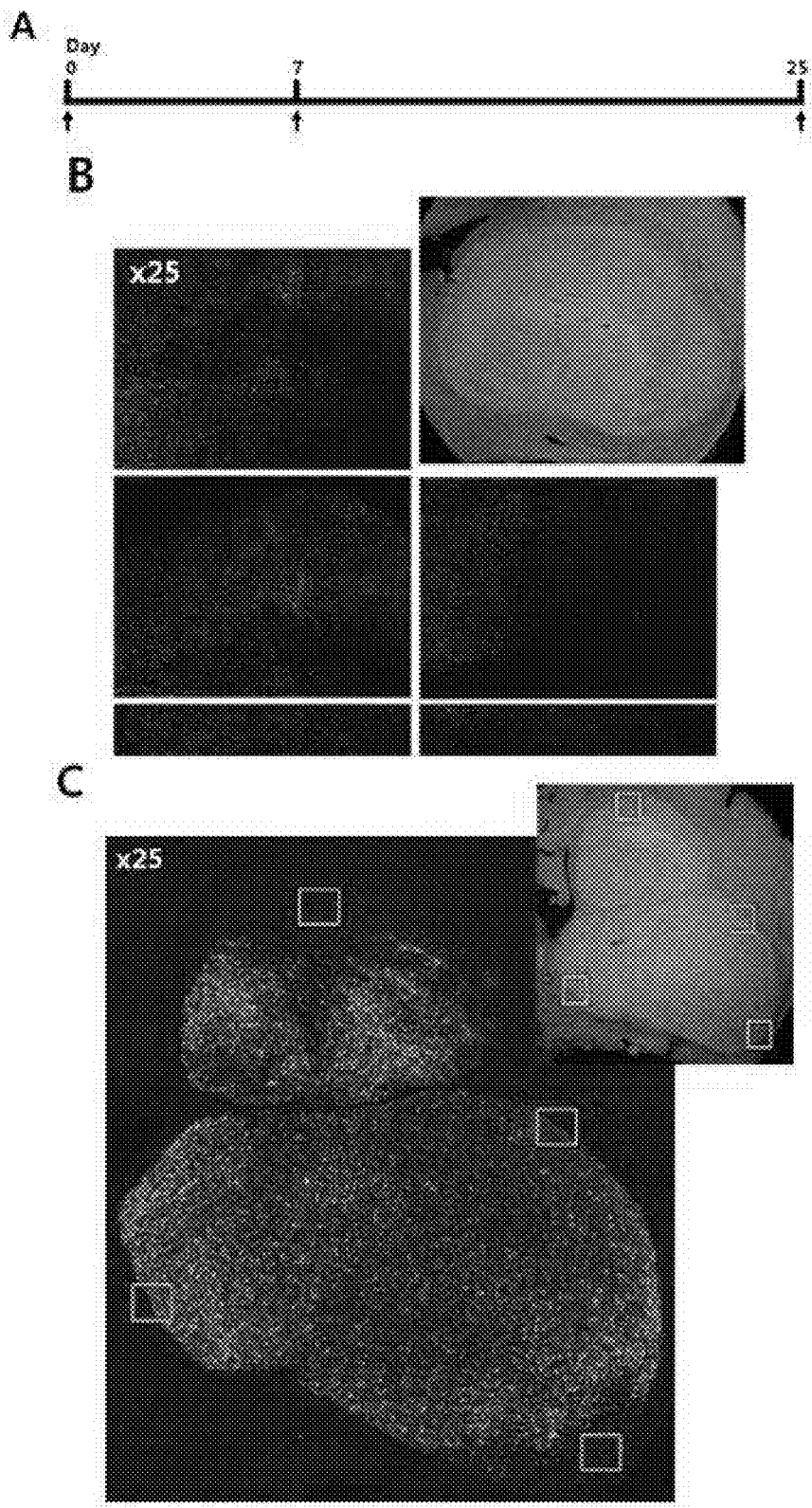

Fluorescence was observed only in cancer cells. That is, the virus was not infected anywhere in the normal brain. The cancer cells infected with the sRCR-FL vector showed very weak fluorescence and were topically infected with the virus, whereas the tumor tissue infected with the spRCR-FL vector showed clearly and entirely expression of fluorescence gene (see FIG. 21).

Example 8

Survival Period of Brain Tumor-Transplanted Nude Mouse Upon spRCR-TK Infection (+GCV Injection)

In the same manner as in described above, a brain striatum of a nude mouse was transplanted with the U-87 MG cells. After 1 week of the tumor transplantation, $1.5 \times 10^7$ gc ($\approx 10^4$ TU)/10 µl of the cancer cells infected with the spRCR-TK vector and 10 µl of PBS (control) were used for intratumoral injection. Then, PBS or GCV (100 mg/kg) was injected intraperitoneally thereto after 21 to 51 days of the tumor transplantation.

Figure 22:
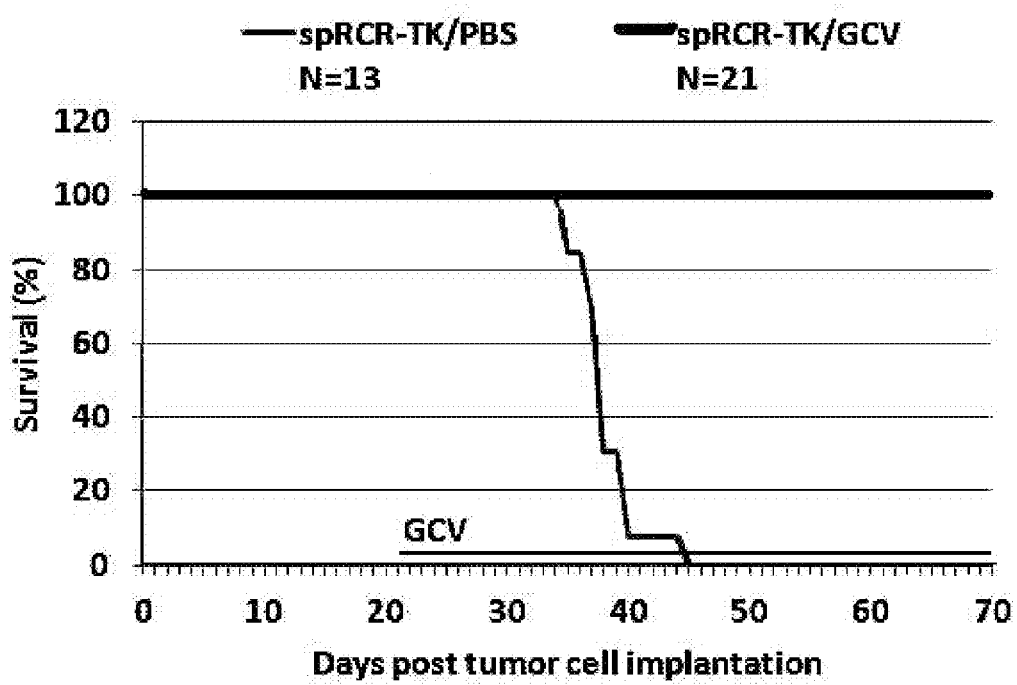
FIG. 22 depicts the results of the survival period obtained after infecting the brain tumor transplanted nude mouse with spRCR-TK vector.

Regarding mice in a control group (N=13), all the mice died around 40 days after the tumor transplantation. Regarding mice in a test group (N=21), 100 mg/kg of GCV was injected to the mice every day, and all the mice survived up to 70 days after the tumor transplantation upon the completion of the observation. Meanwhile, all the mice in the test group maintained their normal body weights (see FIG. 22).

Example 9

Safety of spRCR Vector

A brain striatum of a female, nude mouse aged 6 weeks was transplanted with $3 \times 10^5$ of the U-87MG cells. After 7 days of the transplantation, the $10^7$ gc spRCR-FL vector was injected intratumorally. After 7 days of the injection, the mouse was subjected to perfusion, and the skin was ripped off in sterile conditions from the normal brain next to tumor, tumor, heart, lung, liver, kidney, spleen, intestine, ovary, bone marrow, and a surgical site. Here, a genome DNA was prepared by using the Tissue prep kit (GeneAll).

To perform quantitative PCR, a primer was designed as shown in Table 5 below.

TABLE 5

| Forward Primer | 5'-TCCAGGTAAACTGACAGC-3' |
|---|---|
| Reverse Primer | 5'-CGCCTTTCTAGCCTCTAA-3' |
| FAM probe | 5'-TGTTCTCATCACCCATCAGCCCAC-3' |

Compositions for the PCR reaction include 10 µl of 2×IQ Supermix (2×), 0.4 µl (10 pmol/µl) of sense primer, 0.4 µl (10 pmol/µl) of anti-sense primer, 2 µl (50 ng/µl) of gDNA, 0.03 µl (100 pmol/µl) of FAM probe, and 7.2 µl of sterilized water, resulting in a total volume of 20.03 µl.

In CFX real time PCR C1000 Thermo (Bio-Rad), the PCR was repeating 40 cycles, each of which cycles was performed at a temperature of 95° C. for 30 minutes, at a temperature of 95° C. for 20 seconds, and at a temperature of 58° C. for 60 seconds. Data obtained therefrom were analyzed after the completion of the PCR reaction.

In order to perform a general PCR in the same tissue, 0.5 µg of sample DNA, 0.5 µM of each primer), and 20 µl of 5 units TaKaRa Ex Taq polymerase were prepared and subjected to the PCR by repeating 30 cycles, each of which cycles was performed at a temperature of 94° C. for 1 minute, at a temperature of 60° C. for 30 seconds, and at a temperature of 72° C. for 1 minutes. Here, a primer that recognizes pol and GFP genes of the vector was used. The production was obtained in a size of 3.5 kb, and a sequence of the primer is shown in Table 6 below.

TABLE 6

| Forward primer (pol) | 5'-GGAAAGGACCTTACACAGTC-3' |
|---|---|
| Reverse primer (GFP) | 5'-CGGGTTAACTTACTTGTACAGCTCGTCC-3' |

The PCR product was subjected to electrolysis for 40 minutes in 1% agarose gel at a voltage of 100 V.

Figure 23:
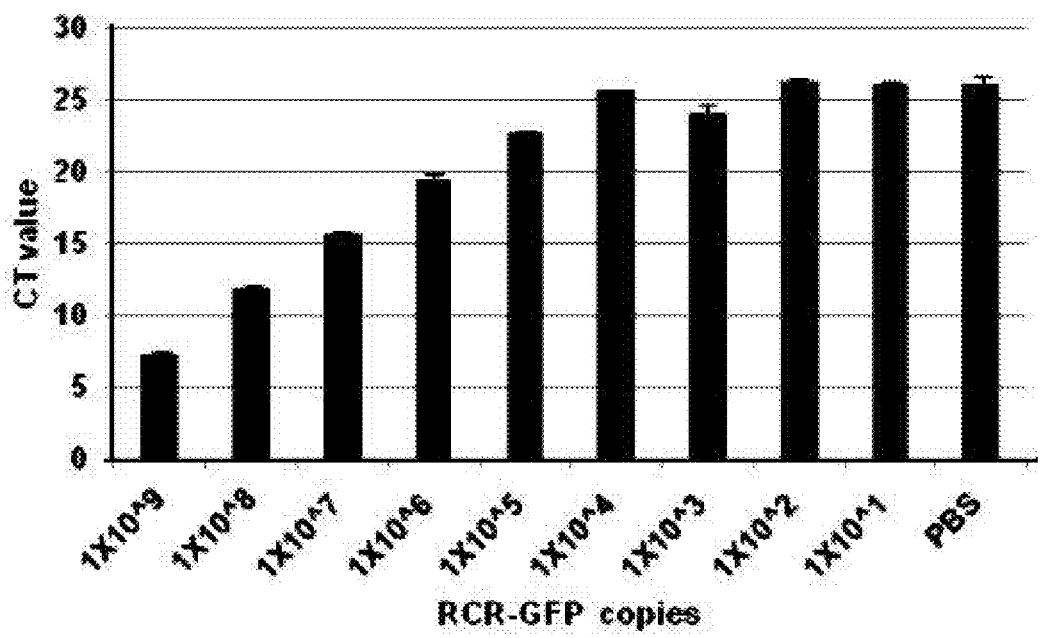
FIG. 23 depicts PCR results obtained by adding a certain number of gene copies to 100 ng of nude mouse genomic DNA to draw a standard curve of the qPCR, and shows data including standard deviation calculated by repeating the experiments 3 times.
Figure 24:
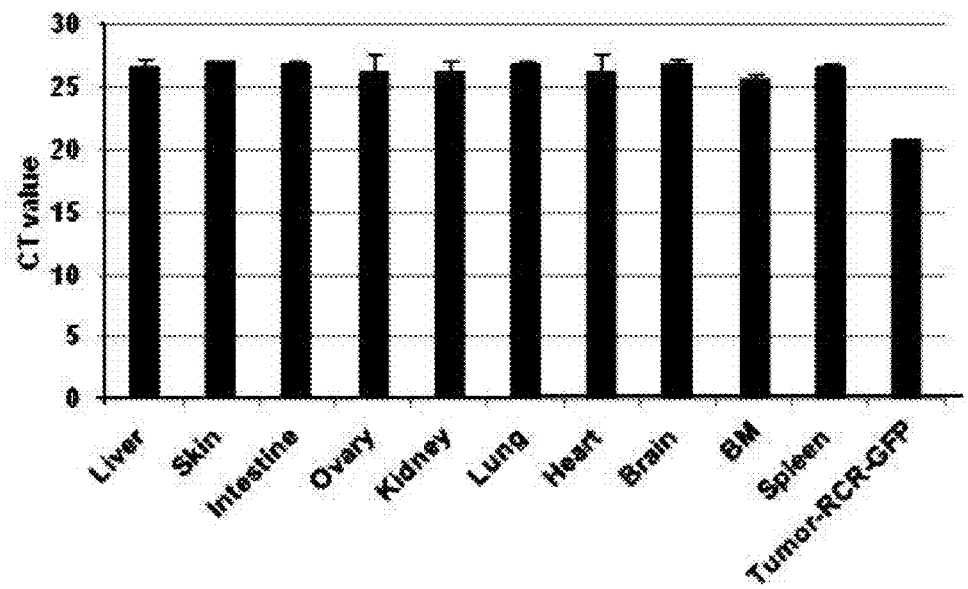
FIG. 24 is a graph showing CT values obtained by performing intratumoral injection of a spRCR-GFP vector into the brain tumor transplanted nude mouse and by performing qPCR using 100 ng of each organ's DNA as a sample. The graph also shows data including standard deviation calculated by repeating the experiments 3 times.
Figure 25:
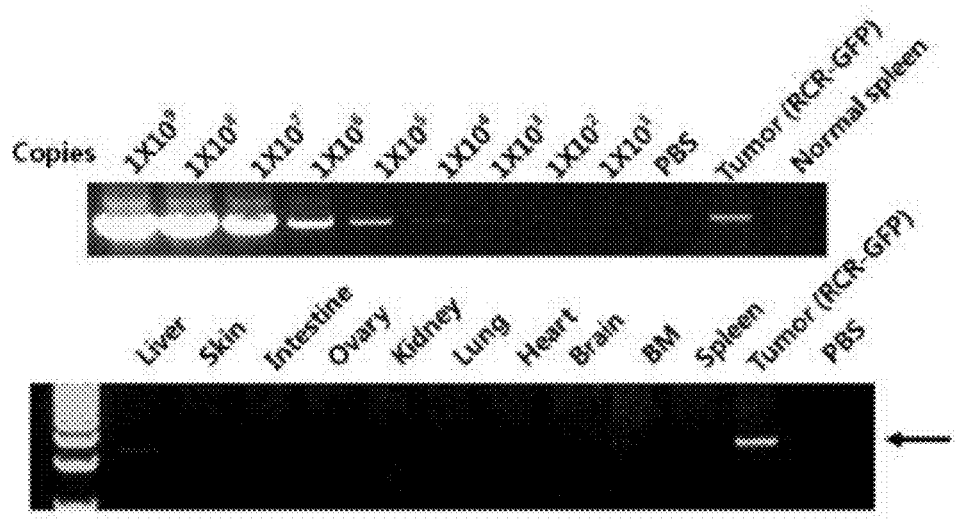
FIG. 25 is an image that confirms the presence of spRCR-GFP genome in 100 ng of the nude mouse genomic DNA by using PCR. The image also shows the results of electrophoresis obtained after performing intratumoral injection of the spRCR-GFP vector into the brain tumor transplanted nude mouse and performing PCR using 100 ng of each organ's DNA as a sample.

The genomic DNA was extracted from the normal brain, tumor tissue, heart, lung, liver, kidney, spleen, intestine, ovary, bone marrow, and a surgical site, or the like, was subjected to qPCR and PCR analysis. As a result, it was confirmed that the GFP sequence was found only in tumor tissues while the GFP sequence was not found in any other tissues (FIGS. 23 to 25).

Example 10

PET-CT Scanning on Mice with HSV-TK Expression in Brain Tumor

In the same manner as in described above, a brain striatum of the nude mouse was transplanted with the U-87 MG cells (n=6). After 7 days of the tumor transplantation, $1.5 \times 10^7$ gc ($\approx 10^4$ TU)/10 µl of the comparative spRCRe-TK vector (replication-defective) or the replication-competent spRCR-TK viral vector was injected intratumorally. After the viral injection, PET-CT scanning was performed on the $3^{rd}$, $7^{th}$, $10^{th}$, $14^{th}$ and $17^{th}$ day of the viral injection. 500 µCi/50 µl of [$^{18}$F]FHBG was injected intravenously (i.v.) to each of the mice, and 1 hour later, the mice were subjected to animal PET-CT (eXplore VISTA CT, GE) scanning. The CT scanning was performed under conditions of 250 µA and 40 KA. The PET scanning was completed by obtaining images for 5 minutes and performing 2D OSEM reconstruction. The images obtained therefrom were then analyzed and implemented by using the Osirix imaging software (The Osirix Foundation, Geneva, Switzerland) (see FIG. 26).

Figure 26:
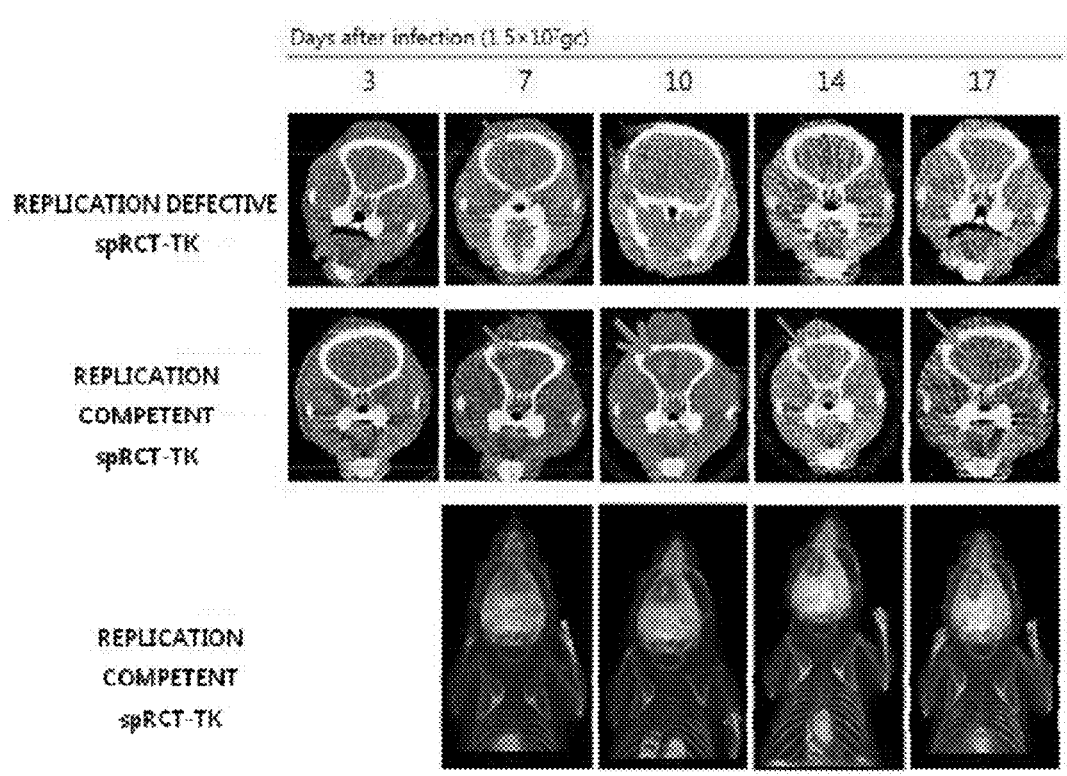
FIG. 26 is PET-CT images showing virus dispersion in cancerous tissues through proliferation of the virus after infecting the brain tumor transplanted nude mouse with the spRCR-TK vector.

As shown in FIG. 26, it was found that the replication-defective virus barely spread in the cancerous tissues while the replication-competent spRCR-TK virus spread in the tumor tissues in a significantly efficient manner.

The invention claimed is:

1. A composition for delivering a gene targeting cells of aberrant proliferation, comprising:
   a retrovirus obtained by transfecting a cell line with a pseudotyped replication-competent retrovirus two-vector system having two separate vectors, said two separate vectors comprise,
   a first recombinant expression vector carrying a murine leukemia virus (MuLV)-Gag gene and a MuLV-Pol gene, the first recombinant expression vector comprising a first vector having a first plasmid map of FIG. 1, and a second recombinant expression vector carrying a gibbon ape leukemia virus (GaLV)-Env gene, the second recombinant expression vector comprising a second vector having a second plasmid map of FIG. 2.

2. The composition of claim 1, wherein the cells of aberrant proliferation comprise cancer cells.

3. The composition of claim 2, wherein the cancer cells are derived from myxoid and round cell carcinomas, locally advanced tumors, metastatic cancer, Ewing's sarcoma, cancer metastasis, lymphatic metastasis, squamous epithelial cell carcinoma, esophagus squamous epithelial cell carcinoma, oral carcinoma, multiple myeloma, acute lymphocytic leukemia, acute non-lymphocytic leukemia, chronic lymphocytic leukemia, chronic myelocytic leukemia, hairy cell leukemia, effusion lymphoma (body cavity based lymphoma), thymic lymphoma lung cancer, small cell carcinoma of the lung, cutaneous T-cell lymphoma, Hodgkin's lymphoma, non-Hodgkin's lymphoma, cancer of the adrenal cortex, ACTH-producing tumor, non-small cell carcinoma of the lung, breast cancer, small cell carcinoma, ductal carcinoma, stomach cancer, colon cancer, colorectal cancer, polyp associated with colorectal neoplasia, pancreatic cancer, liver cancer, bladder cancer, primary superficial bladder tumor, invasive transitional cell carcinomas of the bladder, muscle-invasive bladder cancer, prostate cancer, renal cell carcinoma, esophagus cancer, ovarian carcinoma, uterine cervical cancer, endometrial cancer, choriocarcinoma, ovarian cancer, primary peritoneal epithelial neoplasm, cervical carcinomas, vaginal cancer, cancer of the vulva, uterine cancer, solid tumor in the ovarian follicle, testicular cancer, penile cancer, renal cell carcinoma, brain cancer, head and neck cancer, neuroblastoma, asfrocytic brain tumor, glioma, metastatic tumor cell invasion in the central nervous system, osteoma, osteosarcoma, malignant melanoma, tumor progression of human skin keratinocyte, thyroid cancer, retinoblastoma, neuroblastoma, mesothelioma, Wilms's tumor, gall bladder cancer, trophoblastic neoplasm, hemangiopericytoma, or Kaposi's sarcoma.

4. The composition of claim 1, wherein the cells of aberrant proliferation are non-cancerous cells of aberrant proliferation derived from an inflammatory disease or a hyperproliferative vascular disorder.

5. The composition of claim 4, wherein the non-cancerous cells derived from inflammatory disease are derived from inflammatory-induced bone disease, degenerative arthritis, diabetes, autoimmune myositis, atherosclerosis, stroke, liver cirrhosis, meningitis, inflammatory gastric ulcer, gallbladder stone, kidney stone, paranasal sinusitis, rhinitis, conjunctivitis, asthma, dermatitis, inflammatory bowel disease, inflammatory collagen vascular disease, glomerulonephritis, inflammatory skin disease, rheumatoid arthritis, systemic lupus erythematosus, ankylosing spondylitis, Behcet's disease, ulcerative colitis, Crohn disease, psoriasis, atopic dermatitis, contact dermatitis, moist dermatitis, seborrheic dermatitis, lichen planus, lichen simplex chronicus, pemphigus, bellous pemphigus, epidermolysis bullosa, urticaria, angioedema, vasculitis, erythema, eosinophilia, nummular dermatitis, generalized exfoliative dermatitis, stasis dermatitis, disease of sebaceous gland, perioral dermatitis, pseudofolliculitus barbae, drug rash, erythema multiforme, erythema nodosum, granuloma annulare, or pelvic inflammatory disease (PID).

6. The composition of claim 4, wherein the non-cancerous cells of aberrant proliferation derived from hyperproliferative vascular disorder are derived from vascular sclerosis, atherosclerosis, restenosis and stenosis, vascular malformation, vascular access stenosis associated with blood dialysis, transplant arteriopathy, vasculitis, vascular inflammatory disease, Digeorge syndrome, hereditary hemorrhagic telangeiectasia (HHT), keloid scar, blister disease, hyperproliferative vitreous syndrome, retinopathy of prematurity, myopic choroidal neovascularization, macular degeneration, diabetic retinopathy, neovascularization, primary pulmonary hypertension, asthma, nasal polyps, inflammatory bowel and periodontal disease, endometriosis, ovarian cysts, ovarian hyperstimulation syndrome, arthritis, rheumatoid arthritis, chronic articular rheumatism, synovitis, osteoarthritis, osteomyelitis, osteophytosis, septicemia, or vascular leak syndrome.

7. The composition of claim 1, wherein the first recombinant expression vector and the second recombinant expression vector comprises a foreign-gene-inserted therapeutic gene for treating cancer by killing the cells of aberrant proliferation.

8. The composition of claim 7, wherein,
the cells of aberrant proliferation comprise cancer cells, and
the therapeutic gene comprises at least one selected from an apoptosis-related gene, an apoptosis-inducing gene, an immune gene, an angiogenesis inhibitor gene, and a sequence that expresses shRNA, miRNA, or siRNA that induces gene silencing (RNAi) capable of killing the cancer cells.

9. The composition of claim 8, wherein the apoptosis-related gene activates a prodrug.

10. The composition of claim 9, wherein the apoptosis-related gene comprises thymidine kinase of herpes simplex virus that activates a prodrug, GCV (Ganciclovir).

11. A method of manufacturing a pseudotyped replication-competent retrovirus vector system, the method comprising:
preparing a first recombinant expression vector carrying a MuLV-Gag gene and a MuLV-Pol gene; and
preparing a second recombinant expression vector carrying a GaLV-Env gene.

* * * * *